United States Patent [19]

Kantorovich et al.

[11] Patent Number: 5,426,979
[45] Date of Patent: Jun. 27, 1995

[54] FREQUENCY SPECTRUM APPARATUS FOR DETERMINING MECHANICAL PROPERTIES

[75] Inventors: Edward Kantorovich, Tel Aviv; Alex Rapoport, Rishon Lezion, both of Israel

[73] Assignee: Medicano Systems Ltd., Rishon Lezion, Israel

[21] Appl. No.: 928,272

[22] Filed: Aug. 11, 1992

Related U.S. Application Data

[63] Continuation-in-part of Ser. No. 708,776, May 29, 1991, Pat. No. 5,143,072.

[30] Foreign Application Priority Data

Jun. 4, 1990 [IL] Israel .................................... 94616

[51] Int. Cl.[6] ................................................ A61B 8/00
[52] U.S. Cl. ........................................ 73/628; 73/597; 128/660.02; 128/660.01
[58] Field of Search ............... 73/602, 628, 646, 648, 73/659, 597, 598, 599; 128/660.01, 660.02, 660.07, 661.01, 661.03

[56] References Cited

U.S. PATENT DOCUMENTS

| 3,127,950 | 4/1964 | Itria | 73/597 |
|---|---|---|---|
| 3,228,232 | 1/1966 | Proctor | 73/597 |
| 3,288,241 | 11/1966 | Bancroft et al. | 73/589 |
| 3,372,163 | 3/1968 | Tessandori | 546/49 |
| 3,512,400 | 5/1970 | Lynnworth | 73/597 |
| 3,676,584 | 7/1972 | Plaskas et al. | 73/628 |
| 3,720,098 | 3/1973 | Dixon | 73/597 |
| 3,847,141 | 11/1974 | Hoop | 128/660.01 |
| 4,361,154 | 11/1982 | Pratt, Jr. | 73/597 |
| 4,372,163 | 2/1983 | Tittmann et al. | 73/597 |
| 4,398,421 | 8/1983 | White | 73/597 |

(List continued on next page.)

FOREIGN PATENT DOCUMENTS

| 1159556 | 6/1985 | U.S.S.R. | 128/660.01 |
|---|---|---|---|
| 1172534 | 8/1985 | U.S.S.R. | 128/660.01 |
| 1175435 | 8/1985 | U.S.S.R. | 128/660.01 |
| 1308319 | 5/1987 | U.S.S.R. | 128/660.01 |
| 1342479 | 10/1987 | U.S.S.R. | 128/660.01 |
| 1420383 | 8/1988 | U.S.S.R. | 128/660.01 |
| 9001903 | 3/1990 | WIPO | |

OTHER PUBLICATIONS

T. Nomura et al, "Precise Measurement of Surface Acoustic Wave Velocity Using a Swept Frequency IDT-NDE System", Japanese J. of Applied Physics, Supplements, vol. 27-1, pp. 160-162 (1988).

(List continued on next page.)

*Primary Examiner*—Tom Noland
*Assistant Examiner*—Rose M. Finley
*Attorney, Agent, or Firm*—Abelman, Frayne & Schwab

[57] ABSTRACT

Apparatus for determining, through an interposed medium, the mechanical properties of a solid comprised of more than one material, the solid having a surface. The apparatus includes a) ultrasonic transmission apparatus located in a first location for transmitting ultrasonic waves through the interposed medium and through the solid and generally parallel to the surface, b) at least one ultrasonic receiver unit located in each of second and third locations for receiving the ultrasonic waves, wherein the first, second and third locations are colinear along the surface, c) apparatus for locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location, d) apparatus for receiving a time-based output signal from each of the at least one ultrasonic receiver unit, e) apparatus for transforming at least two of the output signals to the frequency domain thereby to produce frequency domain signals and f) apparatus for determining, from the frequency domain signals, frequency values and their corresponding propagation speeds, for each of the materials within the solid.

4 Claims, 17 Drawing Sheets

U.S. PATENT DOCUMENTS

| | | | |
|---|---|---|---|
| 4,413,517 | 11/1983 | Soden | 73/597 |
| 4,421,119 | 12/1983 | Pratt, Jr. | 73/597 |
| 4,566,459 | 1/1986 | Umemura et al. | 128/660.07 |
| 4,597,292 | 5/1986 | Fujii et al. | 73/599 |
| 4,640,132 | 2/1987 | Flora et al. | 73/602 |
| 4,752,917 | 6/1988 | Dechape | 73/597 |
| 4,774,959 | 10/1988 | Palmer et al. | 128/660.06 |
| 4,896,278 | 1/1990 | Grove | 73/598 |
| 4,913,157 | 4/1990 | Pratt, Jr. et al. | 128/661.03 |
| 4,926,870 | 5/1990 | Brandenburger | 128/660.01 |
| 4,930,511 | 5/1990 | Rossman et al. | 128/661.03 |
| 4,941,474 | 5/1990 | Pratt, Jr. | 128/661.01 |
| 4,947,851 | 8/1990 | Sarvazyan et al. | 73/597 |
| 4,976,267 | 12/1990 | Jeffcott et al. | 128/660.01 |
| 4,982,339 | 1/1991 | Insana et al. | 128/660.01 |
| 4,993,416 | 2/1991 | Ophir | 73/599 |
| 5,029,475 | 7/1991 | Kikuchi et al. | 128/661.03 |
| 5,038,615 | 8/1991 | Trulson et al. | 73/597 |
| 5,038,787 | 8/1991 | Antirch et al. | 128/660.01 |
| 5,042,489 | 8/1991 | Wiener et al. | 126/661.03 |
| 5,143,069 | 9/1992 | Kwon et al. | 128/660.01 |

OTHER PUBLICATIONS

"Inspection, Processing and Manufacturing Control of Metal by Ultrasonic Methods", *Symposium on Ultrasonic Testing*, by C. H. Hastings and S. W. Carter, 52nd Annual Meeting of the American Society for Testing Materials, Jun. 28, 1949, pp. 16–47.

*Wave Motion in Elastic Solids,* by Karl F. Graff, published by the Clarendon Press, Oxford, England in 1975, p. 326.

"Osteoporotic Bone Fragility: Detection by Ultrasound Transmission Velocity," R. P. Heaney et al.; *JAMA*, vol. 261, No. 20, May 26, 1989, pp. 2986–2990.

"Measurement of Velocity of Ultrasound in Human Cortical Bone In Vivo," M. A. Greenfield, et al., *Radiology*, vol. 138, Mar. 1981 pp. 701–710.

"Combined 2.25 MHz ultrasound velocity and bone mineral density measurements in the equine metacarpus and their in vivi applications" R. N. McCartney and L. B. Jeffcott, *Medical and Biological Engineering and Computation*, vol. 25, 1987, Nov. 1877, pp. 620–626.

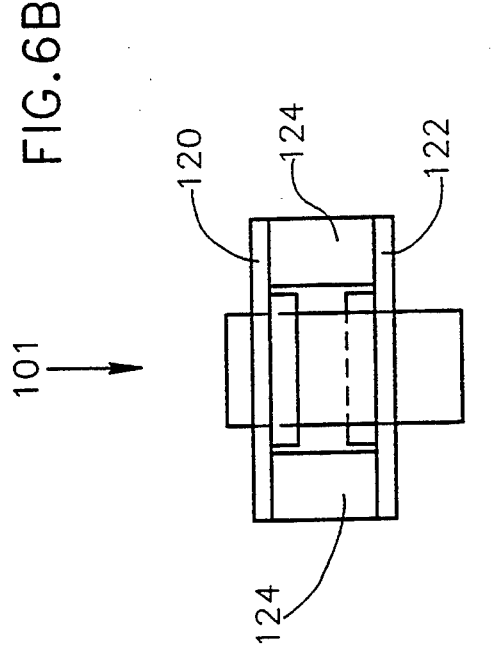
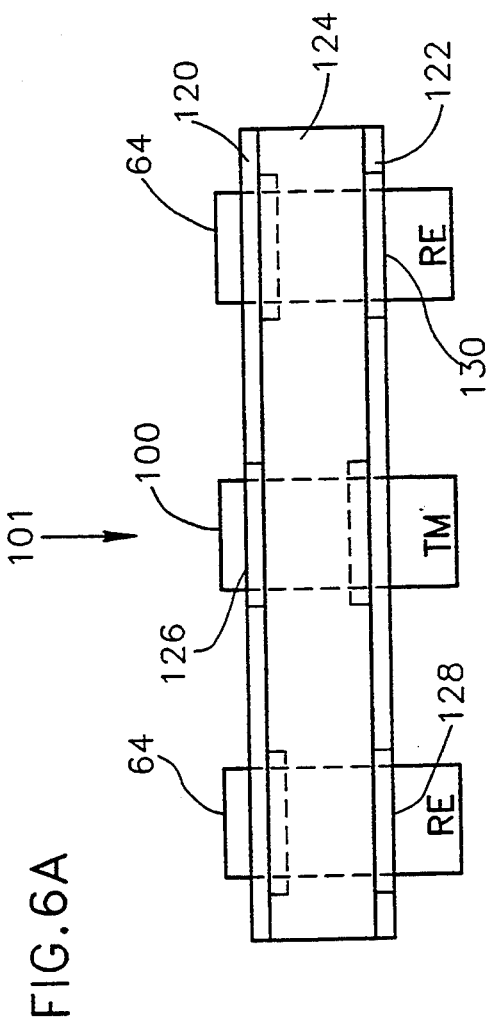
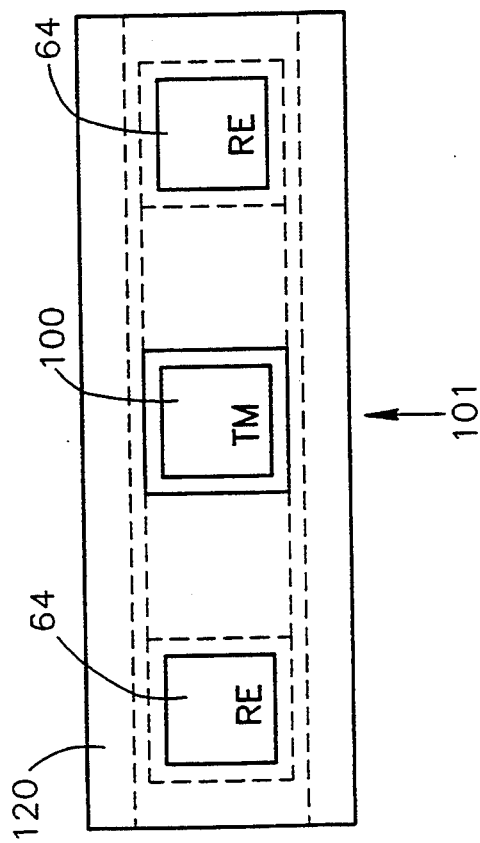

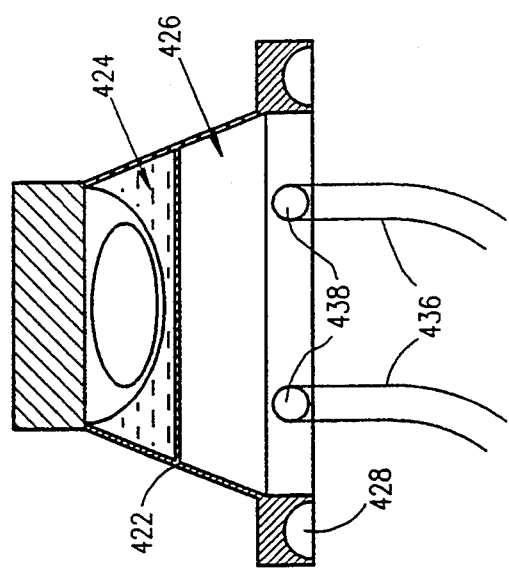
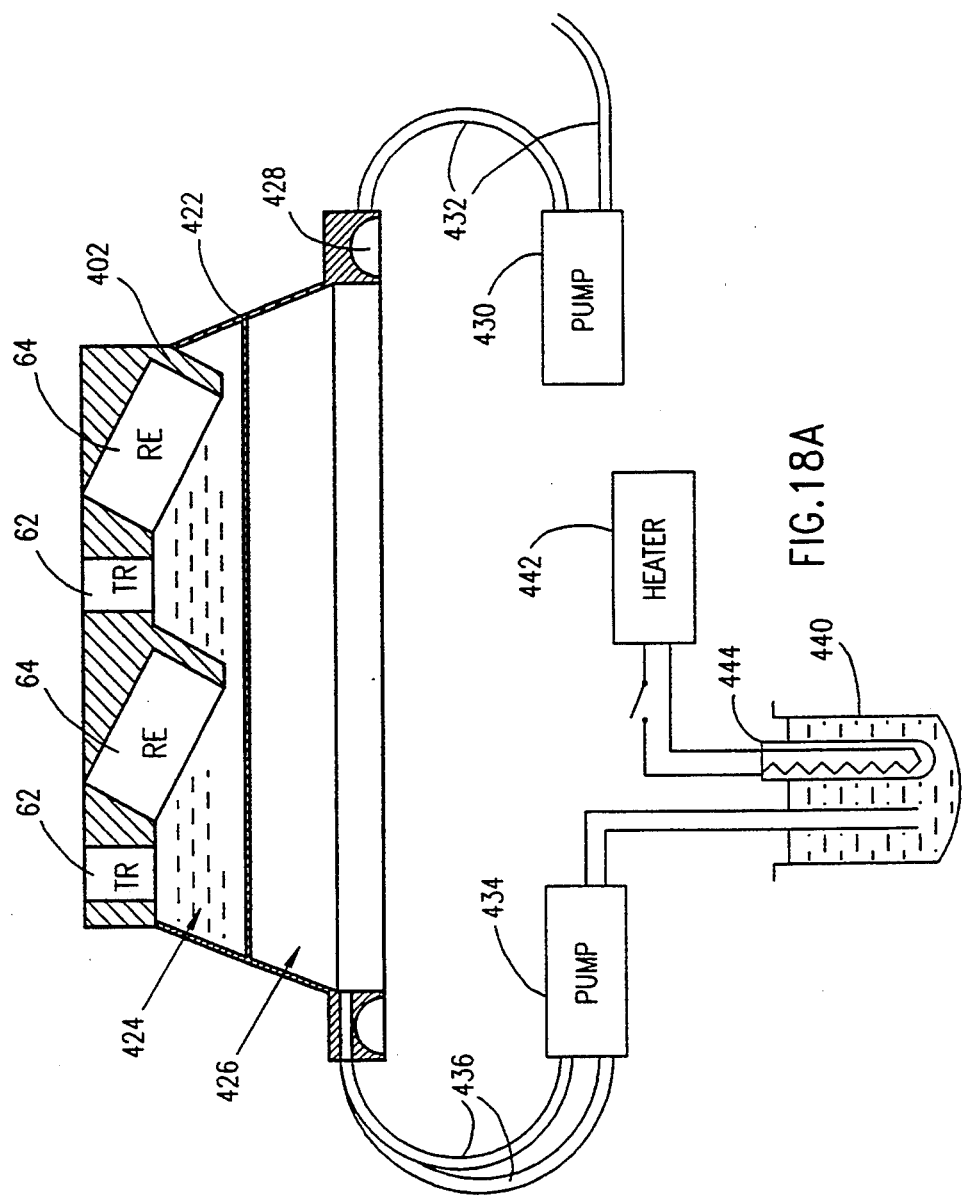
FIG.18B
FIG.18A

FREQUENCY SPECTRUM APPARATUS FOR DETERMINING MECHANICAL PROPERTIES

This application is a continuation-in-part of U.S. patent application Ser. No. 07/708,776, filed May 29, 1991, now U.S. Pat. No. 5,143,072

FIELD OF THE INVENTION

The present invention relates to instrumentation for non-destructive measurement of mechanical properties of materials generally and to instrumentation for non-invasive measurement of the mechanical properties of bone and bone quality.

BACKGROUND OF THE INVENTION

It is known in the art that the velocity of a sound wave in a material depends on the mechanical properties of the material. This is outlined by C. H. Hastings and S. W. Carter in an article entitled "Inspection, Processing and Manufacturing Control of Metal by Ultrasonic Methods", *Symposium on Ultrasonic Testing*, 52 nd Annual Meeting of the American Society for Testing Materials, Jun. 28, 1949, pp. 16-47.

U.S. Pat. Nos. 3,720,098, 3,228,232, 3,288,241, 3,372,163, 3,127,950, 3,512,400, 4,640,132, 4,597,292 and 4,752,917 describe the state of the art of non-destructive testing.

A sound wave which reaches a semi-infinite solid at an angle will typically propagate through the solid as three waves, namely, the longitudinal, transverse and surface waves, wherein each wave has a different velocity. As described by Hastings and Carter, the velocities of the three waves are defined as follows:

$$V_L = \sqrt{\frac{E(1-\sigma)}{\text{rho}(1+\sigma)(1-2\sigma)}} \quad (1)$$

$$V_T = \sqrt{\frac{E}{2(1+\sigma)\text{rho}}} \quad (2)$$

$$V_S = \alpha V_T \quad (3a)$$

$$\alpha = \frac{0.87 + 1.12\sigma}{1+\sigma} \quad (3b)$$

where $V_L$, $V_T$, and $V_S$ are, respectively, the velocities of the longitudinal, transverse and Rayleigh surface waves, and E, $\sigma$ and rho are, respectively, the Young's Modulus, the Poisson's ratio of lateral contraction to longitudinal extension and the mass density of the material. Equation 3b is an empirical relationship as defined on page 326 of *Wave Motion in Elastic Solids*, by Karl F. Graff, published by the Clarendon Press, Oxford England in 1975.

In ultrasonic measurement of the condition of bone, typically only the velocity of the longitudinal wave is used. As defined in the article, "Osteoporotic Bone Fragility: Detection by Ultrasound Transmission Velocity," R. P. Heaney et al,. *JAMA*, Vol. 261, No. 20, May 26, 1989, pp. 2986-2990, the Young's modulus of a bone E is given empirically as:

$$E = K(\text{rho})^2 \quad (4a)$$

and the velocity of sound through the bone is a function of E, where the velocity of sound is typically the longitudinal velocity, as follows:

$$V_L = \sqrt{(E/\text{rho})} = \sqrt{(K \cdot \text{rho})} \quad (4b)$$

where K is a constant which incorporates a number of factors, such as spatial orientation of the bone structures, inherent properties of the bone material and fatigue damage. Thus, the velocity of a longitudinal wave is a function of the mass density and can be used as an indicator of the quality of bone.

The following articles also discuss ultrasonic measurement of bone condition both in vivo and in vitro.

"Measurement of the Velocity of Ultrasound in Human Cortical Bone In Vivo," M. A. Greenfield, et al., *Radiology*, Vol. 138, March 1981, pp. 701-710.

"Combined 2.25 MHz ultrasound velocity and bone mineral density measurements in the equine metacarpus and their in vivo applications," R. N. McCartney and L. B. Jeffcott, *Medical and Biological Engineering and Computation*, Vol. 25, 1987, Nov. 1877, pp. 620-626.

In order to perform in vivo ultrasonically measurements of the mechanical properties of bone, it is necessary to transmit an ultrasonic wave through the soft tissue surrounding the bone. Unfortunately, the thickness of the soft tissue varies along the length of the bone. This can affect the accuracy of the ultrasound propagation time measurement through the bone. In the abovementioned articles, the thickness of the soft tissue is either ignored or an attempt is made to cancel the effects of the soft tissue. In the articles describing in vitro experiments, the soft tissue is removed from the bone.

Russian patents 1,420,383, 1,308,319, 1,175,435, 1,324,479, 1,159,556 and 1,172,534 and U.S. Pat. Nos. 4,926,870, 4,361,154, 4,774,959, 4,421,119, 4,941,474, 3,847,141, 4,913,157 and 4,930,511 describe various systems for measuring the strength of bone based on the velocity $V_L$. These systems typically have one ultrasonic signal transmitter and at least one ultrasonic signal receiver.

Russian patents 1,420,383, 1,308,319 and 1,175,435 solve the problem of the unknown thickness of the soft tissue by assuming values for the thickness of the soft tissue in the area of the measurement or by assuring that the thickness variation is small over the distance between two ultrasonic signal receivers.

Russian patent 1,342,279 utilizes two receivers and a single transmitter and calculates an average group speed through the bone based on the known distance between the two receivers.

Russian patent 1,159,556 defines zones of a bone and the condition of a bone is determined by the difference between the maximum and minimum amplitude of the ultrasound signals measured. It would appear that this measurement is performed on an excised bone.

Russian patent 1,172,534 describes a system which compares the ultrasound signal of a healthy bone with that of an unhealthy bone and from the comparison, produces a diagnosis of the extent of disease in the unhealthy bone.

U.S. Pat. Nos. 4,926,870, 4,421,119 and 3,847,141 describe systems which places a receiver and a transmitter on opposite sides of a bone. U.S. Pat. No. 4,926,870 also compares the resultant signal with a canonical waveform, thereby to identify the health of the bone.

U.S. Pat. Nos. 4,913,157, 4,774,959 and 4,941,474 describe systems which transmit an ultrasonic signal with a spectrum of frequencies.

U.S. Pat. No. 4,930,511 describes a system is placed around a standard inanimate homogeneous material of known acoustic properties before it is placed around a bone.

SUMMARY OF THE INVENTION

The present invention ultrasonically measures mechanical properties of a hard material wherein the ultrasonic signal travels from a transmitter, through a thickness of an interposed medium and through a hard material to be tested, such as a solid. The ultrasonic wave propagates through the hard material as three waves, the longitudinal, transverse and surface waves. From the solid, the ultrasonic wave travels through a second thickness to a first receiver and through a third thickness to a second receiver located a defined distance from the first receiver.

There is therefore provided, in accordance with an embodiment of the present invention, apparatus for determining, through an interposed medium, the mechanical properties of a solid comprised of more than one material, the solid having a surface. The apparatus includes a) ultrasonic transmission apparatus located in a first location for transmitting ultrasonic waves through the interposed medium and through the solid and generally parallel to the surface, b) at least one ultrasonic receiver unit located in each of second and third locations for receiving the ultrasonic waves, wherein the first, second and third locations are colinear along the surface, c) apparatus for locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location d) apparatus for receiving a time-based output signal from each of the at least one ultrasonic receiver unit, e) apparatus for transforming at least two of the output signals to the frequency domain thereby to produce frequency domain signals and f) apparatus for determining, from the frequency domain signals, frequency values and their corresponding propagation speeds, for each of the materials within the solid.

Additionally, in accordance with an embodiment of the present invention, the apparatus includes apparatus for determining, from a difference of the frequency domain signals, extent of attenuation of each of the materials within the solid.

Furthermore, there is provided, in accordance with an alternative embodiment of the present invention, the apparatus of the present invention includes a) ultrasonic transmission apparatus located in a first location for transmitting ultrasonic waves through the interposed medium and through the solid and generally parallel to the surface, b) at least one ultrasonic receiver unit located in each of second and third locations for receiving the ultrasonic waves, wherein the first, second and third locations are colinear along the surface, c) apparatus for locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location, d) apparatus for receiving a time-based output signal from each of the at least one ultrasonic receiver unit and for determining a first peak of each of the output signals and e) apparatus for calculating from the first peaks, the ,extent of attenuation of the ultrasonic waves by the solid.

There is alternatively provided, in accordance with an embodiment of the present invention, apparatus for determining, through an interposed medium, the mechanical properties of a solid having a surface. The apparatus includes a) ultrasonic transmission apparatus located in a first location for transmitting ultrasonic waves through the interposed medium and through the solid and generally parallel to the surface, b) at least one ultrasonic receiver unit located in each of second and third locations for receiving the ultrasonic waves, wherein the first, second and third locations are colinear along the surface, c) apparatus for locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location and d) apparatus for estimating a thickness of the solid from output of the at least one receiver unit in response to two transmissions by the ultrasonic transmission apparatus.

In accordance with another embodiment of the present invention, the apparatus of the present invention includes a) a housing, b) an acoustic barrier, c) ultrasonic transmission apparatus, located in a first location on a first side of the acoustic barrier, for transmitting ultrasonic waves through the interposed medium and through the solid and generally parallel to the surface, d) first and second ultrasonic receiver units, located in each of second and third locations on a second side of the acoustic barrier, for receiving the ultrasonic waves, wherein the first, second and third locations are colinear along the surface, e) apparatus for moving the housing such that a first receipt time of an ultrasonic wave from the surface to the first ultrasonic receiver unit at the second location is generally equivalent to a second receipt time from the surface to the second ultrasonic receiver unit at the third location and f) apparatus for calculating the mechanical properties from ultrasonic waves transmitted by the ultrasonic transmission apparatus once the first and second receipt times are generally equivalent.

Still further, in accordance with an embodiment of the present invention, the apparatus of the present invention includes a) a housing, b) ultrasonic transmission apparatus located in a first location for transmitting ultrasonic waves through the interposed medium and through the solid and generally parallel to the surface, c) first and second ultrasonic receiver units located within the housing in each of second and third locations for receiving the ultrasonic waves, wherein the first, second and third locations are colinear along the surface and d) a flexible membrane attached to the housing at one end and forming a closed section and an open section, the closed section being filled with a coupling material, the flexible membrane having a vacuum hole at a second end thereof. When the apparatus is placed onto human skin and air within the vacuum hole is evacuated, the apparatus is sealingly coupled with the human skin.

Moreover, in accordance with a further alternative embodiment of the present invention, the apparatus of the present invention includes a) a flexible array of piezoelectric cells formable into at least one ultrasonic transmitter and at least one ultrasonic receiver, b) apparatus for defining a first plurality of the piezoelectric cells in a first location as the at least one ultrasonic transmitter and at least second and third pluralities of piezoelectric cells, in second and third locations, respectively, as the at least one ultrasonic receiver, and c) apparatus for calculating the mechanical properties from ultrasonic waves transmitted by the ultrasonic transmitter. The first, second and third locations are colinear along the surface, and the ultrasonic transmitter transmits ultrasonic waves through the interposed medium and through the solid in a direction generally parallel to the surface.

Additionally, in accordance with an embodiment of the present invention, the apparatus described above also includes apparatus for defining the at least one receiver unit such that a first receipt time of an ultrasonic wave from the surface to the at least one ultrasonic receiver unit at the second location is generally equivalent to a second receipt time from the surface to the at least one ultrasonic receiver unit at the third location.

There is still further provided, in accordance with an embodiment of the present invention, a method of scanning, through an interposed medium, a solid having a surface and for determining therefrom the mechanical properties of the solid. The method includes the steps of a) defining a first plurality of transducer cells in a first location as at least one ultrasonic transmitter and at least second and third pluralities of transducer cells, in second and third locations, respectively, as at least one ultrasonic receiver, b) calculating the mechanical properties from ultrasonic waves transmitted by the ultrasonic transmitter and c) repeating the steps of defining and calculating for different locations on the solid. The first, second and third locations are colinear along the surface and the ultrasonic transmitter transmits ultrasonic waves through the interposed medium and through the solid in a direction generally parallel to the surface.

Additionally, in accordance with an embodiment of the present invention, the method includes the step of defining the at least one receiver unit such that a first receipt time of an ultrasonic wave from the surface to the at least one ultrasonic receiver unit at the second location is generally equivalent to a second receipt time from the surface to the at least one ultrasonic receiver unit at the third location, and wherein the step of repeating is performed in randomly chosen locations.

Alternatively, in accordance with an embodiment of the present invention, the step of repeating is performed in sequentially chosen locations and wherein the step of calculating includes the step of determining the mechanical properties from knowledge of the velocity of the ultrasonic waves through the interposed medium.

There is provided, in accordance with the present invention, a further method for determining, through an interposed medium, the mechanical properties of a solid comprised of more than one material, the solid having a surface. The further method includes the steps of a) transmitting ultrasonic waves from a first location through the interposed medium and through the solid and generally parallel to the surface, b) receiving the ultrasonic waves with at least one ultrasonic receiver unit located in each of second and third locations, wherein the first, second and third locations are colinear along the surface, c) locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location, d) receiving a time-based output signal from each of the at least one ultrasonic receiver unit, e) transforming at least two of the output signals to the frequency domain thereby to produce frequency domain signals and f) determining, from the frequency domain signals, frequency values and their corresponding propagation speeds, for each of the materials within the solid. The method can also include the step of determining, from a difference of the frequency domain signals, extent of attenuation of each of the materials within the solid.

In accordance with the present invention, a further method is provided. The further method includes the steps of a) transmitting ultrasonic waves from a first location through the interposed medium and through the solid and generally parallel to the surface, b) receiving the ultrasonic waves from at least one ultrasonic receiver unit located in each of second and third locations, wherein the first, second and third locations are colinear along the surface, c) locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location, d) receiving a time-based output signal from each of the at least one ultrasonic receiver unit and for determining a first peak of each of the output signals and e) calculating from the first peaks, the extent of attenuation of the ultrasonic waves by the solid.

Finally, in accordance with an embodiment of the present invention, there is also provided a method for determining, through an interposed medium, the mechanical properties of a solid having a surface. The method includes the steps of a) transmitting ultrasonic waves from a first location through the interposed medium and through the solid and generally parallel to the surface, b) receiving the ultrasonic waves with at least one ultrasonic receiver unit located in each of second and third locations, wherein the first, second and third locations are colinear along the surface, c) locating the at least one receiver unit such that a first receipt time of an ultrasonic wave from the surface to the at least one ultrasonic receiver unit at the second location is generally equivalent to a second receipt time from the surface to the at least one ultrasonic receiver unit at the third location and d) estimating a thickness of the solid from output of the at least one receiver unit in response to two transmissions by the ultrasonic transmission means.

BRIEF DESCRIPTION OF THE DRAWINGS

The present invention will be understood and appreciated more fully from the following detailed description taken in conjunction with the drawings in which:

FIG. 6A, 6B and 6C is a schematic illustration of an acoustically insulating element useful in the apparatus of FIG. 5;

FIGS. 18A and 18B are schematic side and front view illustrations respectively, of an alternative embodiment of a portion of the apparatus of FIG. 3;

DETAILED DESCRIPTION OF PRESENT INVENTION

Figure 1:
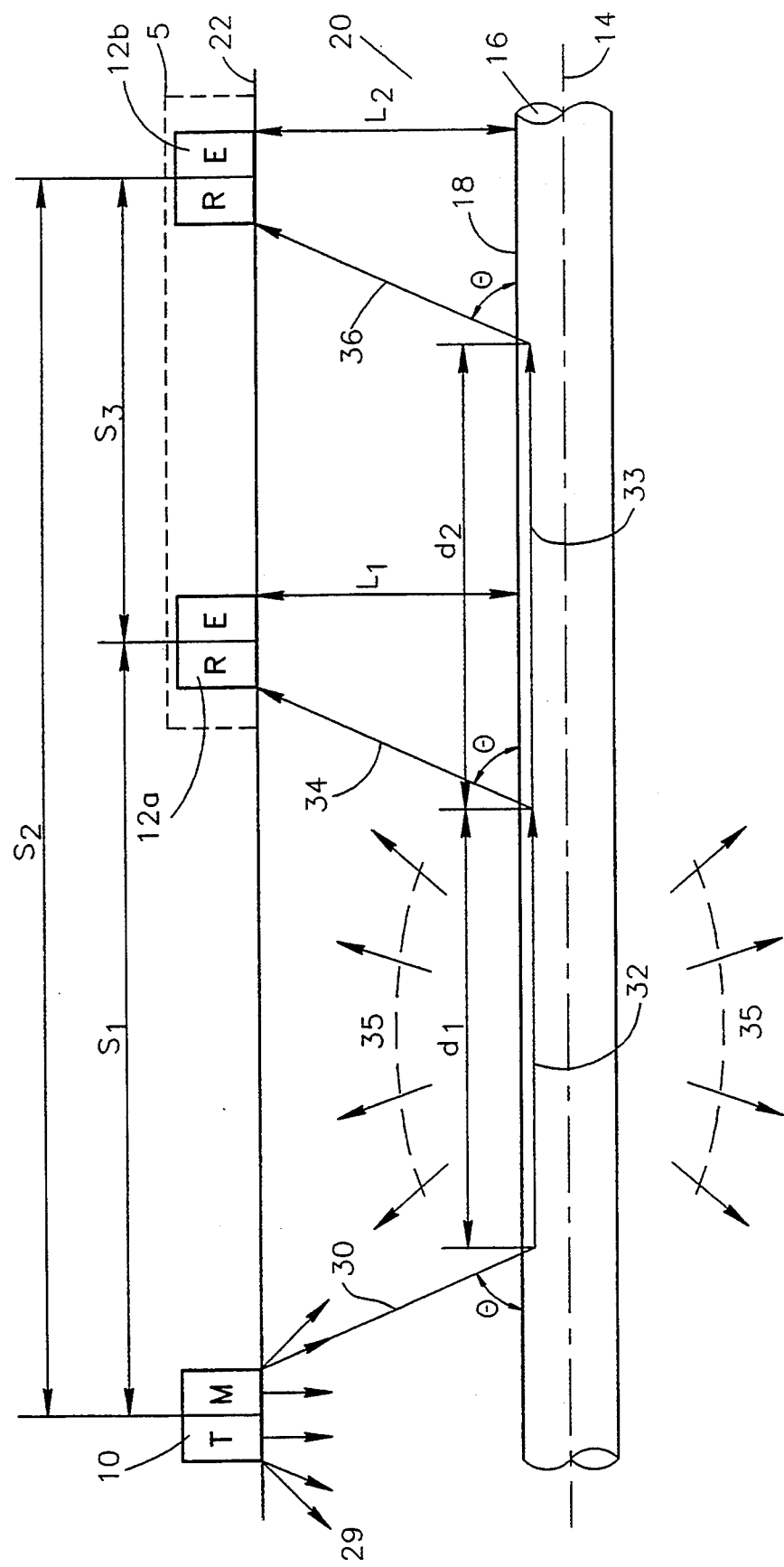
FIG. 1 is a schematic illustration of a method of ultrasonically measuring mechanical properties of materials operative in accordance with the present invention.

Reference is now made to FIG. 1 which schematically illustrates a method of ultrasonically measuring mechanical properties of a hard material, such as a solid 16, and apparatus which implements the method constructed and operative in accordance with the present invention. The apparatus comprises an ultrasonic transmitter 10, such as an ultrasonic transducer made of piezoelectric ceramics, typically capable of transmitting ultrasonic signals at frequencies in the range of 20 KHz to 10 MHz, and a receiver unit 5 for receiving the transmitted signals. Unit 5 typically comprises at least two ultrasonic receivers 12 such as ultrasonic transducers made of piezoelectric ceramics.

The unit 5 and transmitter 10 are placed generally in the direction of a long axis 14 of solid 16 and preferably parallel to a surface 18 of solid 16. Solid 16 is typically a metal whose mechanical properties, such as Young's Modulus (E), density (rho) and Poisson's ratio ($\sigma$), are to be measured. It can also be skeletal bone.

Along surface 18 of the solid 16 is typically an interposed medium 20, such as a gel or water for a metal solid 16 or such as soft tissue typically surrounding skeletal bone. The transmitter 10 and receivers 12 are typically placed on a top surface 22 of the interposed medium 20 wherein the receivers are located at distances $s_1$ and $s_2$ from transmitter 10. In accordance with the present invention, thicknesses $L_1$ and $L_2$ of the interposed medium 20 under each of receivers 12 are preferably generally equivalent.

In accordance with an alternative embodiment of the present invention, the interposed medium 20 is not utilized and the transmitter 10 and receivers 12 are placed directly on surface 18 of solid 16.

The transmitter 10 typically transmits an ultrasonic wave 29 which propagates through the interposed medium 20 as a longitudinal wave until it reaches surface 18. A portion of wave 29, marked by arrow 30, reaches surface 18 at an angle $\Theta$ to surface 18 where $\Theta$ is the Brewster Angle. As is known in the art, the wave 29 generates in solid 16 three waves, the longitudinal, transverse and surface waves, schematically marked by arrow 32. As is known in the art, if the hard material is not a solid 16, only the longitudinal wave will be propagated.

The three waves propagate through solid 16 and generate longitudinal waves 35 in interposed medium 20 to be received by receivers 12.

Portions of waves 35, marked by arrows 34 and 36, propagate through interposed medium 20 at angle $\Theta$ with respect to surface 18. As is known in the art, the path marked by arrows 30, 32 and 34 is the shortest path an ultrasonic wave can take to reach a first one of receivers 12, marked 12a. The shortest path to reach a second one of receivers 12, marked 12b, is marked by arrows 30, 32, 33 and 36. Thus, a wave propagating along the paths marked by arrows 30, 32, 34 or 30, 32, 33 and 36 will be received first; other waves propagating along other paths will be received later.

The Brewster angle e is calculated as follows:

$$\Theta = \arccos(V_L'/V_L) \qquad (5)$$

where $V_L'$ is the velocity of a longitudinal wave in interposed medium 20 and $V_L$ is the velocity of a longitudinal wave in hard material 16. For soft tissue, $V_L'$ is on average 1540 m/s and for bone, $V_L$ is on average 3500m/s, producing a Brewster angle $\Theta$ of roughly 65°.

The first ultrasonic wave to reach receiver 12a is a longitudinal wave which leaves solid 16 at the Brewster Angle $\Theta$ after traveling through solid 16 for a distance $d_1$. The first ultrasonic wave to reach receiver 12b is a longitudinal wave which travels through solid 16 for a distance $d_1 + d_2$.

It will be appreciated that the three waves do not reach a receiver 12 at the same time due to their different velocities. This is illustrated in FIGS. 2A and 2B, to which reference is now briefly made. FIG. 2A illustrates a signal 40, representing the ultrasonic wave transmitted by transmitter 10, and signals 42, 44 and 46 which are received by receiver 12a and represent the longitudinal, transverse and surface waves, respectively.

Signal 40 is produced for a time tau, where tau is typically fairly short, so as to enable a separation between the longitudinal, transverse and surface waves. For example, 5 cycles of a 1 MHz signal will produce a tau of 5 microseconds.

Signals 42, 44 and 46 comprise low energy portions 41, 43 and 45, respectively, corresponding to the first waves to reach receivers 12 which typically have much less energy compared to the later signals. In accordance with the present invention and in contrast to the prior art, propagation times $t_{L1}$, $t_{T1}$ and $t_{S1}$ are measured from the initiation of signal 40 (i.e. the beginning of transmission of ultrasonic wave 29) to the moment the first waves reach receivers 12. The prior art measures a propagation time $t_p$ measured from the initiation of signal 40 to the moment signal 42 reaches a significant amplitude. Propagation time $t_p$ measures the time of propagation of a reflected signal, rather than one propagated through solid 16.

As is known in the art, the larger the distance between the transmitter 10 and a receiver 12, the longer are the times $t_{L1}$, $t_{T1}$, $t_{S1}$ and the more separated are the signals 42, 44 and 46. The size of the distance $d_1$ necessary to produce a separation among the signals 42, 44 and 46 depends on the mechanical properties of the solid 16 and for bone are typically at least 5 cm.

It will be appreciated that the minimum value for $s_1$ depends on the thicknesses $L_1$ and $L_2$; the bigger $L_1$ and $L_2$ are, the bigger $s_1$ has to be to ensure that $d_1$ is greater than 0. In other words, there has to be some propagation through the solid 16. It will also be appreciated that $d_2$ has to be large enough to achieve accurate measurements and small enough to ensure that the signals 52, 54 and 56 have not overly decreased in power due to absorption of the signal energy by solid 16. Typically, $d_2$ is a few cm.

FIG. 2B is similar to FIG. 2A and illustrates signals 52, 54 and 56 received by receiver 12b. Signals 52, 54 and 56 respectively comprise .Low energy portions 51, 53 and 55. It will be appreciated that each of low energy portions 51, 53 and 55 are received slightly later than each of low energy portions 41, 43 and 45, respectively. The propagation times are marked $t_{L2}$, $t_{T2}$ and $t_{S2}$.

The velocity of propagation of each of the longitudinal, transverse and surface waves can be calculated by taking a known distance, such as the distance from receiver 12a and 12b, $s_3 = s_2 - s_1$, and dividing by the propagation time through that distance. The propagation time through $s_3$ is calculated for the longitudinal wave as follows.

The propagation time $t_{L1}$ is a combination of propagation times $t_{30}$, $t_{30}$ and $t_{34}$ for the waves marked by arrows 30, 32 and 34, respectively, and the propagation time $t_{L2}$ is a combination of propagation times $t_{30}$, $t_{32}$, $t_{33}$ and $t_{36}$ for the waves marked by arrows 30, 32, 33 and 36, respectively. Written mathematically, this becomes equations 6a and 6b.

$$t_{L1} = t_{30} + t_{30} + t_{34} \tag{6a}$$

$$t_{L2} = t_{30} + t_{30} + t_{33} + t_{36} \tag{6b}$$

If the thicknesses $L_1$ and $L_2$ of the interposed medium 20 under receivers 12 are generally equivalent and because the angle to both receivers 12 is $\theta$, the propagation time through the interposed medium 20 to the receivers 12 will be equivalent, or $$t_{34} = t_{36} \tag{7}$$

Taking the difference between equations 6a and 6, and including equation 7 produces $$t_{L2} - t_{L1} = t_{33} \tag{8}$$

Simple geometry states that if the thicknesses $L_1$ and $L_2$ are generally equivalent and since the angle of propagation of the waves marked by arrows 34 and 36 is equivalent, the distances $d_2$ and $s_3$ will be generally equivalent. Therefore, $$V_L = s_3/(t_{L2} - t_{L1}) \tag{9}$$

Similarly, $$V_T = s_3/(t_{T2} - t_{T1}) \tag{10}$$

$$V_S = s_3/(t_{S1} - t_{S1}) \tag{11}$$

Thus, equations 1-2 can be solved to produce the Poisson's ratio $\sigma$ and a ratio E/rho as follows.

$$\sigma = \frac{B - 2}{2(B - 1)} \tag{12}$$

$$\frac{E}{rho} = \frac{V_L^2 (3B - 4)}{B(B - 1)} \tag{13}$$

or $$\frac{E}{rho} = 2V_T^2 \left| 1 + \frac{B - 2}{2(B - 1)} \right| \tag{14}$$

where $$ti\ B = (V_L/V_T)^2 \tag{15}$$

Figure 3:
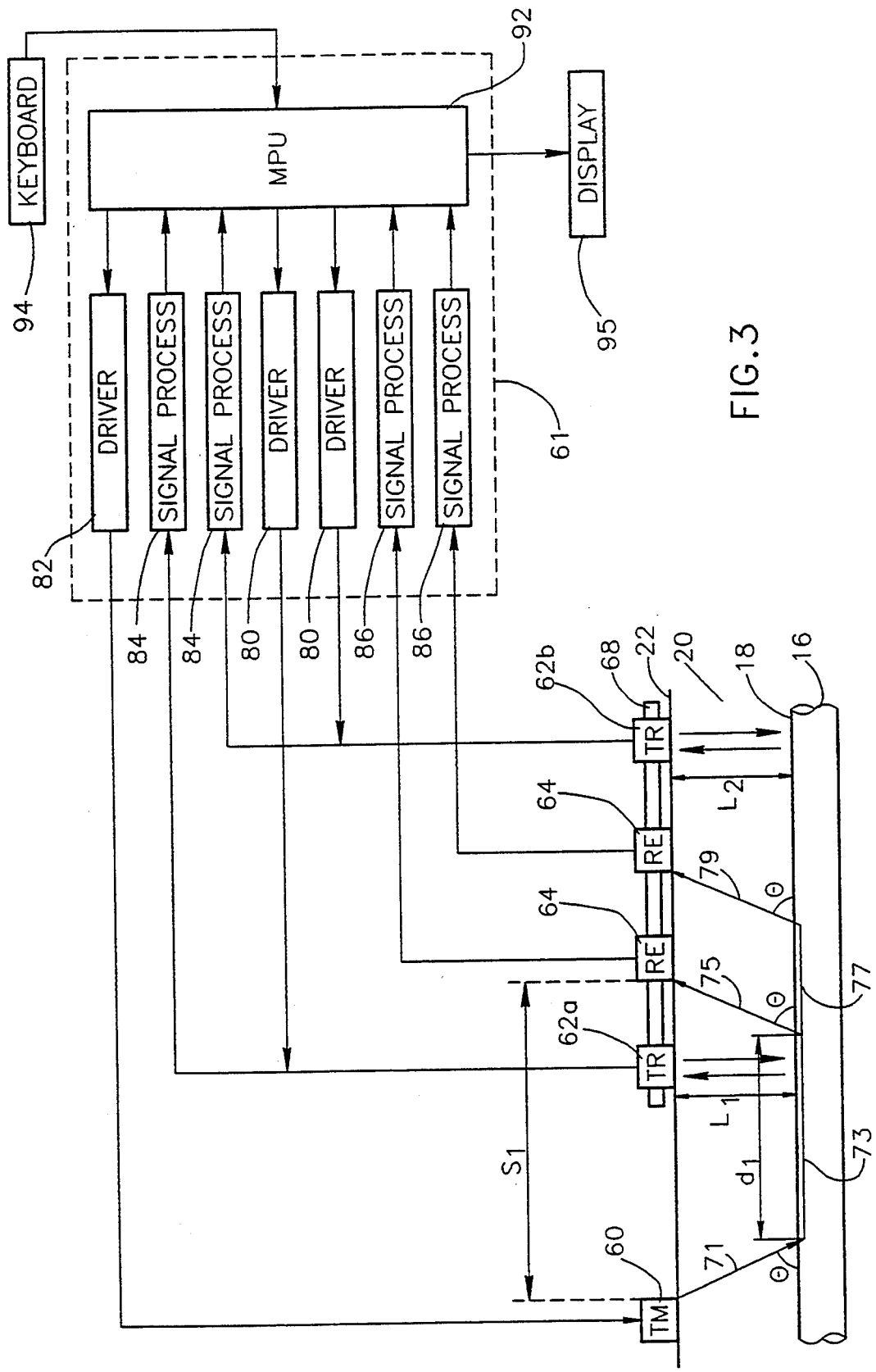
FIG. 3 is a part block diagram, part schematic illustration of in vivo ultrasonic apparatus for mechanical property measurement utilizing the method of FIG. 1.

Reference is now made to FIG. 3 which illustrates apparatus for in vivo measuring of the mechanical properties of a solid, such as bone, which is surrounded by an interposed medium, such as soft tissue, of unknown and non-constant thickness, constructed and operative in accordance with a ]preferred embodiment of the present invention.

Figure 9:
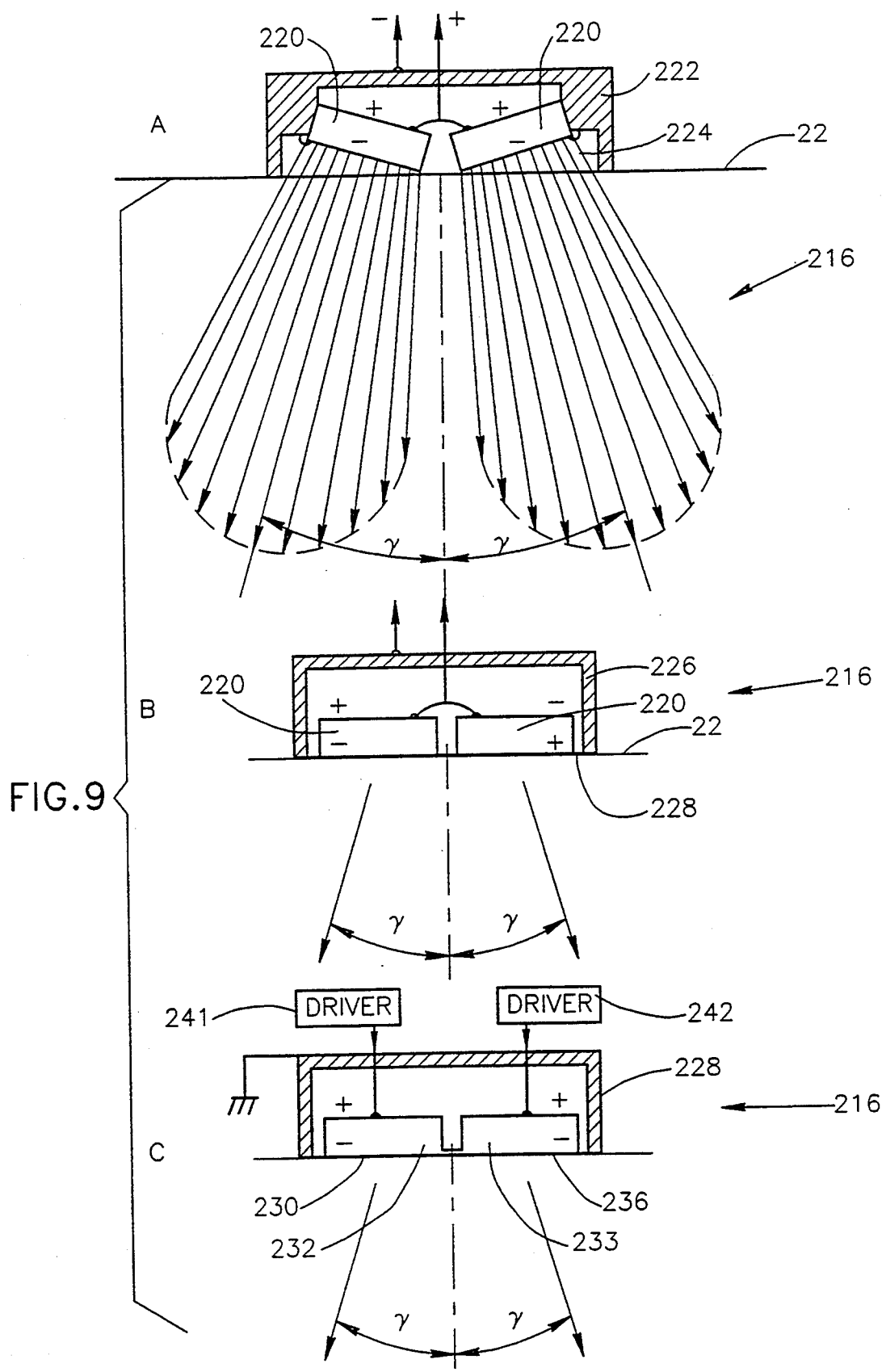
FIGS. 9A–9C are schematic illustrations of transmitters useful in the embodiments of FIGS. 3 and 5.

The apparatus for in vivo measuring typically comprises an ultrasonic transmitter 60, typically transmitting in the range 20 KHz-10 MHz, for transmitting an ultrasonic wave 71, at least two ultrasonic transmitter-receivers 62 transmitting typically in the range 20 KHz-10 MHz, for estimating the thickness of the interposed medium 20 surrounding a solid 16, a plurality of ultrasonic receivers 64 for receiving the ultrasonic signal transmitted by the transmitter 60 and a processing unit 61. Preferred embodiments for transmitter 60 and receivers 64 are shown in FIGS. 9A-9C.

The two transmitter-receivers 62 and the receivers 64 are typically combined in a unit located such that there is a distance $s_1$ between the transmitter 60 and a first receiver 64. Typically, the receivers 64 are located between the transmitter-receivers 62. Thus, if the thickness of the interposed medium 20 surrounding the solid 16 is generally equivalent under the transmitter-receivers 62, it is equivalent under the plurality of receivers 64.

In accordance with a preferred embodiment of the present invention, the two transmitter-receivers 62 are operative to transmit an ultrasonic wave in a direction generally perpendicular to the surface 22 of the interposed medium 20 and to receive the reflection of the transmitted wave from surface 18. The transmitter-receivers 62 and the receivers 64 are pressed into the interposed medium 20 so as to change their locations with respect to the solid 16 until the received signals have propagated in the interposed medium 20 for the same length of time.

Additionally, transmitter-receivers 62 are operative to estimate the thickness $L_1$. The estimate of $L_1$ is useful in estimating the distance $s_1$, useful in defining the placement of transmitter 60. Through geometric considerations, $s_1$ is approximated as follows:

$$s_1 \sim d_1 + 2L_1/\tan \Theta \qquad (16)$$

Since, as mentioned hereinabove, the distance $d_1$ must be greater than 0, $s_1$ is calculated to be larger then $2L_1/\tan \Theta$, typically by 30–40%. Alternatively, $s_1$ can be a fixed distance from the receivers 64.

Figure 4:
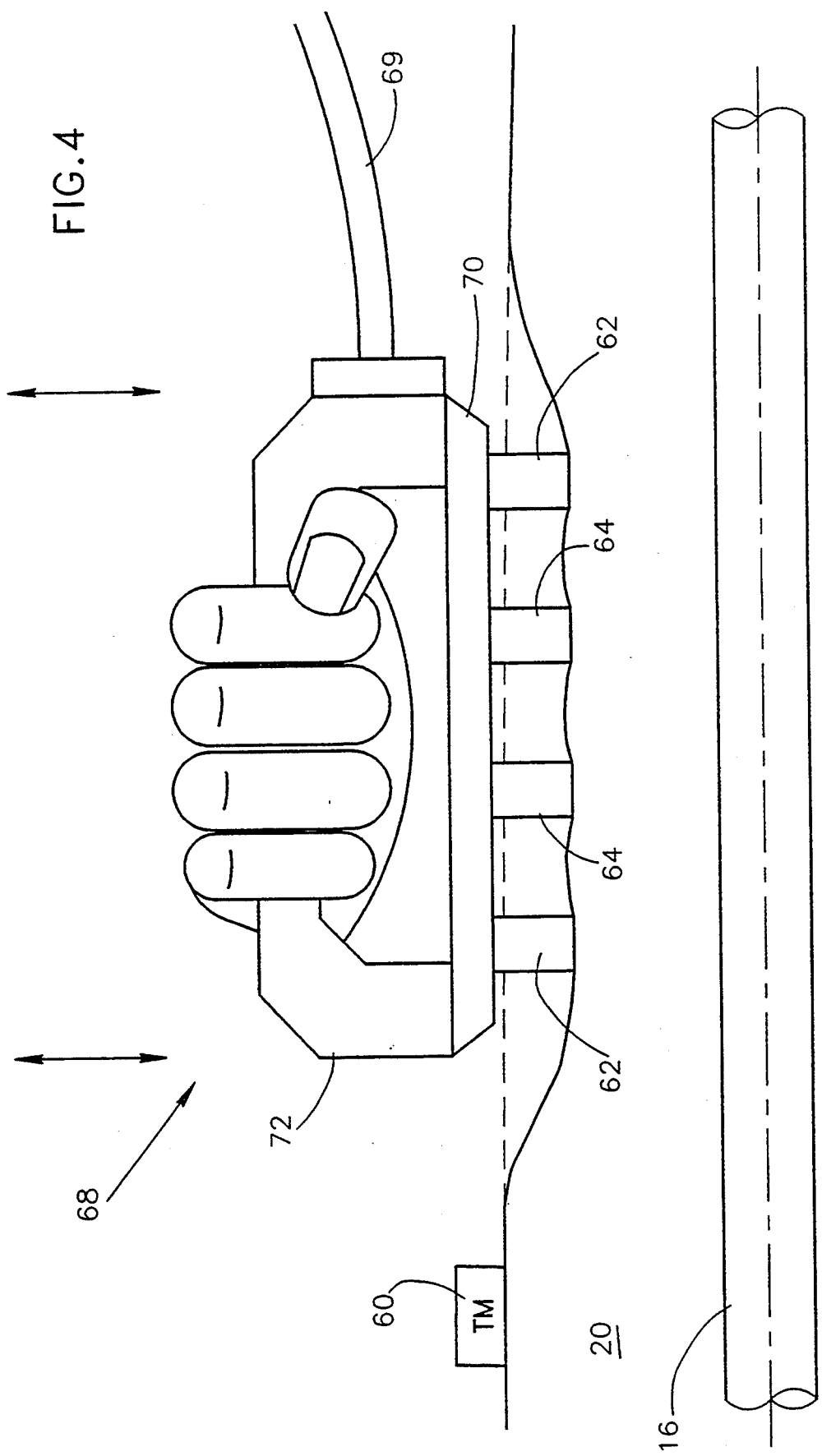
FIG. 4 is a pictorial illustration of apparatus for ensuring that ultrasonic transducers are parallel to a surface of a material to be measured useful in the apparatus of FIG. 3.

To effect the change in location of the transmitter-receivers 62 and the receivers 64, the elements 62 and 64 are combined together in a single rockable unit 68 as shown in FIG. 4 to which reference is now briefly made. The elements 62 and 64 are held together in a unit 70 to which is attached a rocking unit 72, such as a handle, to rockingly press the elements 62 and 64 into the interposed medium 20. By "rockingly press" it is meant that the rocking unit 72 is slowly rocked from side to side while pressing into the interposed medium 20. Attached to the rockable unit 68 are cables 69 for connecting the rockable unit 68 to the processing unit 61.

It will be appreciated that rockable unit 68 can be any suitable unit, whether manually or automatically operated.

It will also be appreciated that rockable unit 68 can be slidingly moved along surface 22 while measurements are performed, as described hereinbelow. Accordingly, measurements along the solid 16 can be taken, giving an operator an indication of locations of changes or discontinuities in the quality of the material of solid 16.

While the rockable unit 68 is being rocked, the transmitter-receivers 62 continually transmit and receive ultrasonic waves. The received signals are sent to the processing unit 61 which continually measures receipt times of the two received signals, where a receipt time is the time to measure the thicknesses $L_1$ and $L_2$. When the difference between the receipt times of the two received signals is generally zero, indicating that the thickness of the interposed medium 20 between the two transmitter-receivers 60 and the solid 16 is generally equivalent, the processing unit 61 causes the transmitter 60 to transmit an ultrasonic wave, marked by arrow 71.

Receivers 64 receive the ultrasonic wave after it has passed through the interposed medium 20 and the solid 16, as shown by arrows 73, 75, 77 and 79. Processing unit 61 receives the received signals, calculates at least $t_{L1}$ and $t_{L2}$, and from them, calculates $V_L$ which is correlated to the mechanical properties of bone, as defined in Equation 4b. Additionally, processing unit 61 can calculate the ratio E/rho and $\sigma$ from equations 12–15.

It will be appreciated that the transmission and reception of the ultrasonic signals occurs within typically 200 microseconds so that any changes due to rocking of the rockable unit 70 have generally no effect on the thickness of the interposed medium 20 under the receivers 64 during the measurement.

Reference is made back to FIG. 3. The processing unit 61 comprises drivers 80 and 82 for driving ultrasonic transmitter-receivers 62 and transmitter 60, respectively, and signal processor units 84 and 86 for processing the received signals from transmitter-receivers 62 and from receivers 64, respectively.

Processing unit 61 additionally comprises a Main Processing Unit (MPU) 92, such as a microcontroller, for controlling the apparatus through sending driving signals to drivers 80 and 82 and receiving and processing signals from signal processor units 84 and 86. MPU 92 additionally interfaces with an operator of the apparatus of the present invention through a keyboard 94 and a display 95.

If $s_1$ is not fixed, at the beginning of a measurement, it is approximated as follows. Rockable unit 68 is rockingly pressed into interposed medium 20 while MPU 92 pulses transmitter-receivers 62 and receives signals from them via signal processor units 84 using the larger threshold level $T_2$. When $delta_{13} t$, the time difference between the receipt times of the received signals, is generally zero, MPU 92 calculates the time $t_{tr}$, between the transmission and receipt of each signal sent by and reflected to each transmitter-receiver 62. By multiplying $t_{tr}$ by the known average velocity of sound in soft tissue, MPU 92 calculates $L_1$ which is then used in equation 17 for defining the distance $s_1$.

To take a measurement, the rockable unit 68 is again rockingly pressed into interposed medium 20 while MPU 92 alternates, at a high frequency, between pulsing one transmitter-receiver, marked 62a, and the other transmitter-receiver, marked 62b. It receives the processed signals from signal processor units 84 and calculates a time difference delta_t between the receipt times of the received signals from transmitter-receivers 62. When delta_t is generally zero, MPU 92 pulses driver 82 to produce the ultrasonic wave marked by arrow 71 and stops pulsing drivers 80.

The ultrasonic wave produces ultrasonic waves, marked by arrows 75 and 79, which are received by receivers 64. The received signal is processed by signal processors 86 and the output is sent to MPU 92 for evaluation of at least the time difference $t_{L2} - t_{L1}$ and for calculation of at least the velocity $V_L$, in accordance with equation 9.

Figure 2:
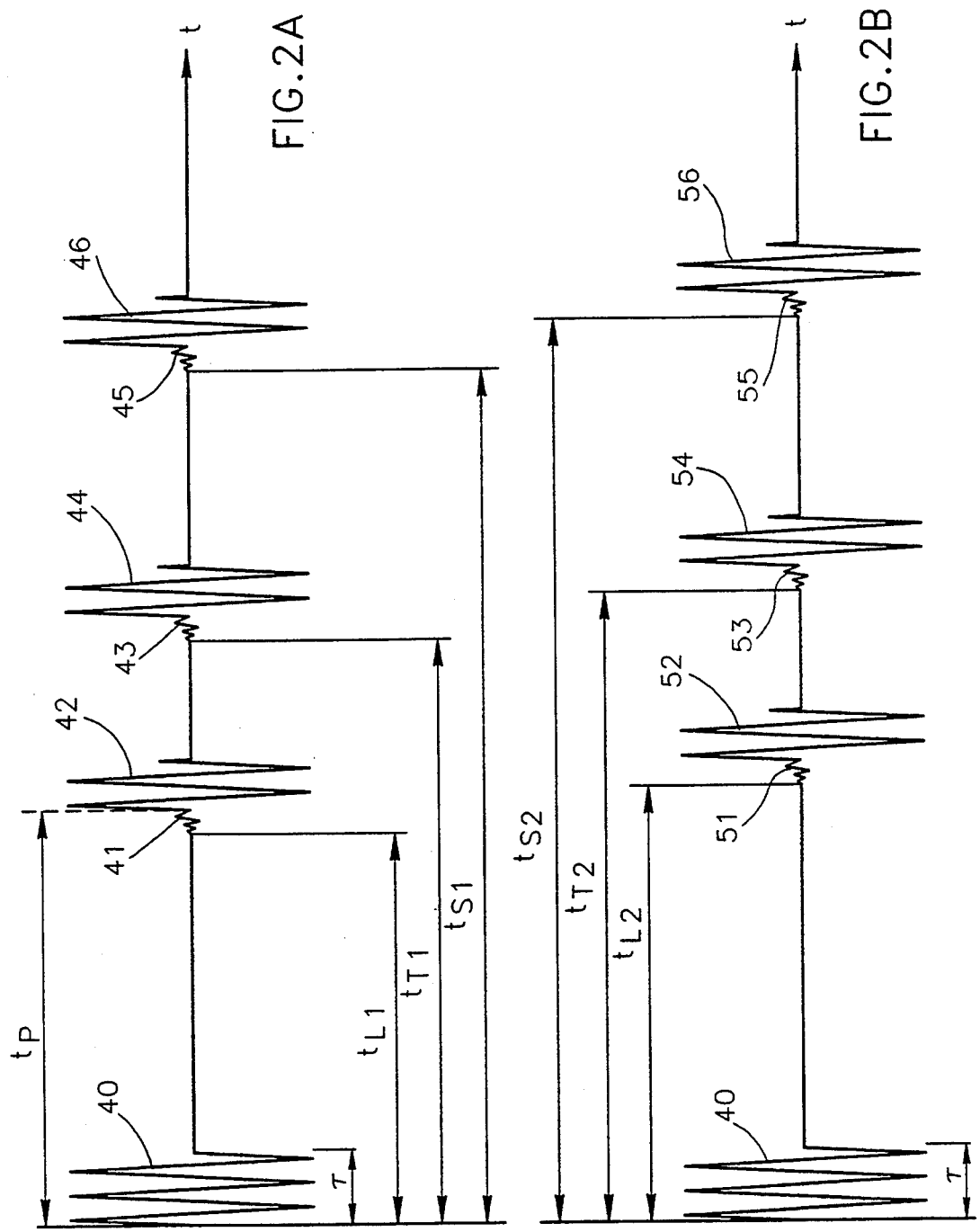
FIGS. 2A and 2B are graphic illustrations of ultrasonic signals transmitted and received by ultrasonic transducers using the method of FIG. 1.

It will be appreciated that the apparatus of the present invention is operative to calculate $V_S$ and $V_T$ also, utilizing the method outlined hereinabove with respect to FIGS. 1 and 2. From the calculation of $V_L$, $V_S$ and $V_T$, the ratio E/rho and can be calculated. It will be noted, however, that the calculation of $V_L$ is necessary for comparing the results of the apparatus of the present invention with results of other prior art devices.

Reference is now made to FIGS. 7 and 8A–8D which respectively illustrate the elements of signal processor unit 84 or 86 and their operation.

Figure 8:
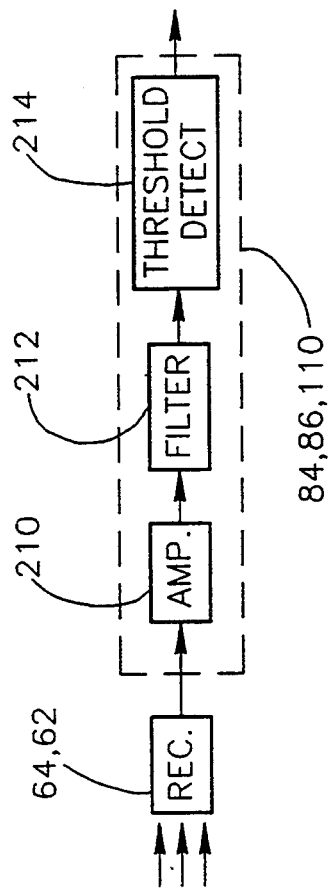
FIGS. 8A–8D are graphical illustrations indicating the output signals from elements of the signal processor of FIG. 7.

In order to measure the moment the first waves reach receivers 64, signal processor unit 84 or 86 comprises an automatic gain control amplifier 210 of high sensitivity and low noise/signal ratio for exponentially amplifying signals 42 and 52 so as to measure the initiation of portions 41 and 51 and to compensate for the typical exponential attenuation of ultrasonic signals. The output of the amplifier 210 is shown in FIG. 8B for an input signal 42 of FIG. 8A where signal 42 comprises a low energy portion 41.

Signal processor unit 84 or 86 additionally comprises a band pass filter 212 for filtering out all signals not in the range of frequencies transmitted by transmitter 60, thereby to reduce noise in the received signal produced by the amplification or otherwise. Its output is shown in FIG. 8C for the input signal of FIG. 8B.

Furthermore, each signal processor unit 84 and 86 comprises a threshold detector 214 for identifying the initiation of either signals 42 and 52 or portions 41 and 51, respectively. Thus, threshold levels $T_1$ and $T_2$, shown in FIG. 8C, are defined. $T_1$ identifies the portions 41 and 51 and $T_2$ identifies the signals 42 and 52. The output of threshold detector 214 is shown in FIG. 8D for an input signal of FIG. 8C.

Figure 5:
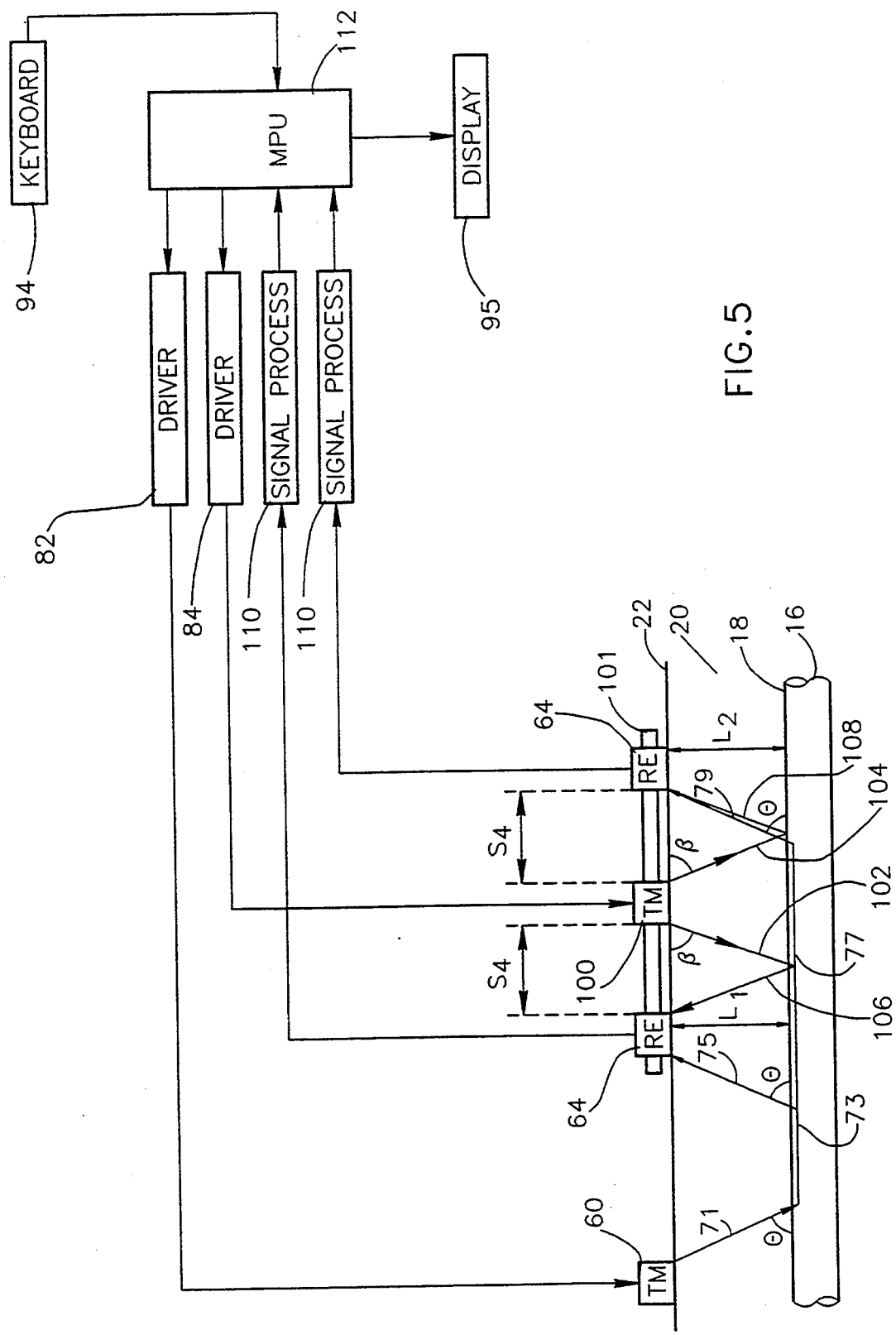
FIG. 5 is a part block diagram, part schematic illustration of an alternative embodiment of the apparatus of FIG. 3.

Reference is now made to FIG. 5 which illustrates an alternative embodiment: of the apparatus of FIG. 3. In this embodiment, the two transmitter-receivers 62 are replaced, by a single transmitter 100, described in more detail hereinbelow with reference to FIGS. 9A–9C, located exactly equidistant between an even plurality of receivers 64. Transmitter 100 and at least two receivers 64 area connected together via, an acoustically insulated unit 101. Unit 101 is shown in detail in FIGS. 6A–6C.

Transmitter 100 transmits at least two ultrasonic waves at a general direction having a non-zero angle gamma (FIGS. 9A–9D) with respect to a perpendicular axis of surface 22 (not shown). A portion of the two waves, marked 102 and 104 in FIG. 5 and having an angle $\beta$ as shown, are reflected from solid 16 to receivers 64 as waves 106 and 108. The angle $\beta$ is unknown and depends on the thicknesses $L_1$ and $L_2$.

Receivers 64 receive reflections 106 and 108, from the surface 18, and send the received signal to signal processors 110, similar to signal processors 84 and 86 of the embodiment of FIG. 3, for processing with both threshold level $T_1$ and $T_2$. The processed signal is then sent to a MPU 112, similar to MPU 92 of the embodiment of FIG. 3.

If $s_1$ is not fixed, at the beginning of a measurement, it is approximated as follows. Unit 101 is rockingly pressed into interposed medium 20 while MPU 112 pulses transmitter 100 and receives signals from receivers 64 via signal processor units 110 using the larger threshold level $T_2$. When delta_t, the time difference between the receipt times of the received signals, is generally zero, MPU 112 calculates the time $t_{tr}$, similar to time tp of FIG. 2A, between the transmission and receipt of each signal sent by transmitter 100 and received by receivers 64.

Once $t_{tr}$ is calculated, the thickness $L_1$ is approximated as follows:

$$L_1 = \sqrt{[(V_L' * t_{tr}/2)^2 - (s_4/2)^2]} \quad (17)$$

where $s_4$ is the distance between transmitter 100 and a receiver 64. Since, as mentioned hereinabove, the distance $d_1$ must be greater than 0, $s_1$ is calculated, in accordance with equation 16, to be larger then $2L_1/\tan\Theta$, typically by 30–40%.

During a measurement, unit 101 is again rockingly pressed into interposed medium 20 while MPU 112 pulses transmitter 100 and receives signals from receivers 64 via signal processor units 110, using t he larger threshold level $T_2$. When delta_t is generally zero, MPU 112 pulses driver 82 to produce the ultrasonic wave marked by arrow 71 and stops pulsing driver 84.

The ultrasonic wave produces ultrasonic waves, marked by arrows 75 and 79, which are received by receivers 64. The received signal is processed by signal processors 110, Using threshold level T1, and the output is sent to MPU 112 for evaluation of at least the time difference $t_{L2} - t_{L1}$ and for calculation of at least the velocity $V_L$, in accordance with equation 9.

Reference is now made to FIGS. 6A–6C which are side, top and end view illustrations of the acoustically insulated unit 101. The transducers 64 and 100 of FIG. 5 are enclosed in two rigid frames 120 and 122, typically of metal, between which is an acoustically absorbent material 124, such as elastic rubber. Receivers 64 are attached to frame 120 and transmitter 100 is attached to frame 122, wherein frame 120 has a hole 126 in which transmitter 120 sits .and frame 122 has holes 128 and 130 in which sit receivers 64.

The material 124 is operative to absorb ultrasonic waves which are transmitted by transmitter 100 such that receivers 64 do not receive such waves before receipt of the ultrasonic waves propagated through the solid 16. Frames 120 and 122 are operative to provide a firm shape to material 124. Each frame only holds one type of ultrasonic transducer; for example, frame 120 holds only receivers 64.

Unit 101 is necessary to ensure that the ultrasonic wave transmitted by transmitter 100 is received by receivers 64 only after having propagated through solid 16. Without the acoustic insulation provided by unit 101, it is possible that the first signals received by receivers 64 are those from wave which propagated through frames 120 and 122.

Reference is now made to FIGS. 9A–9C which illustrate preferred embodiments of an ultrasonic transceiver 216 operative as transmitters 60 and 100 and receivers 64. Transceiver 216 is operative to transmit an ultrasonic wave 71 at an angle gamma and to receive energy which arrives generally in that direction thereby increasing the amount of energy available in low energy portions 41 and 51.

Ultrasonic transceiver 216 is configured to produce ultrasonic waves in two directions, marked by angles gamma, and generally no wave in the direction perpendicular to the surface 22 on which transceiver 216 stands. Typically, gamma = 90 − $\Theta$.

In FIG. 9A, transceiver 216 comprises two standard ultrasonic transducers 220 having positive and negative terminals, denoted by + and − signs, respectively, whose positive terminals are connected together. Transducers 220 are housed in a housing 222 comprising two angled portions 224 on which sit transducers 220. The angled portions 224 are typically comprised of an acoustically transmissive material, such as gel. In this embodiment, the negative terminals are connected to ground and the positive terminals are connected to a driver.

A second embodiment of transceiver 216 is shown in FIG. 9B. As in the previous embodiment, transceiver 216 comprises two standard transducers 220 enclosed in a housing, labeled 226. In this embodiment, the positive terminal of one transducer 220 is connected to the negative terminal of the other, and vice versa. As is known in the art, this produces waves having opposite phases; thus, only the waves generally at an angle gamma are produced. One positive-negative terminal pair is placed on an electrode 228 which is typically placed along surface 22. The other positive-negative terminal pair, which is connected to a driver, is located inside housing 226. The housing 226 is connected to ground.

FIG. 9C illustrates a third embodiment of transceiver 216 which is housed in a housing 228 and is comprised of a single ultrasonic transducer 230 which is at least partially cut into two sections 232 and 233. The negative terminals of sections 232 and 233 are typically attached to an electrode 236 and the positive terminals of sections 232 and 233 are connected to opposite polarity drivers 240 and 241 such that section 232 receives a positive signal at the same time that section 233 receives a negative signal, and vice versa.

It will be appreciated that what has been described herein is merely illustrative of the method and apparatus of the present invention. Other methods of achieving the same goal are included in the present invention. For example, an alternative method for defining $s_1$ is as follows.

In FIG. 2A, signal 42 is typically produced by ultrasonic waves reflecting from the surface 18 of solid 16 and portion 41 is produced by waves propagating a distance $d_1$ through the solid 16. Thus, if there is a difference between the receipt time $t_{L1}$ of portion 41 and the receipt time $t_p$ of signal 42 then $d_1$ is greater than 0 as required. Measurement of $t_{L1}$ and $t_p$ merely requires that signal processors 86 and 100 have the two threshold levels $T_1$ and $T_2$.

It will be appreciated that the apparatus of the present invention is operative for thicknesses of an interposing medium 20 which are not equivalent, although the results are less accurate. Referring once again to FIG. 1, if the receipt times $t_{L1}$ and $t_{L2}$ differ by the measured value delta__t, then equations 6–8 are rewritten as follows into equations 18–20:

$$t_{L1} = t_{30} + t_{32} + t_{34} \quad (18a)$$

$$t_{L2} = t_{30} + t_{32} + t_{33} + t_{36} \quad (18b)$$

where $$t_{34} = t_{36} + \text{delta\_t} \quad (19)$$

and delta__t might be positive or negative. Thus, $$t_{L2} - t_{L1} = t_{33} + \text{delta\_t} \quad (20)$$

Since, due to geometric considerations, if $L_1$ is not equivalent to $L_2$ then $d_2$ is not necessarily equivalent to $s_3$. However, $$L_1 = L_2 + \text{delta\_L} = L_2 + (\text{delta\_t})(V_L') \quad (21)$$

and therefore $$d_2 = \sqrt{(s_3^2 - (\text{delta\_L})^2} \quad (22)$$

and $$V_L = d_2/(t_{L2} - t_{L1}) \quad (23)$$

It will further be appreciated that the apparatus of the present invention is operative without an interposing medium 20. For such a situation, Unit 5 (FIG. 1) comprises only one receiver 12a and the equations 9–11 are:

$$V_L = s_1/t_{L1} \quad (24)$$

$$V_T = s_1/t_{T1} \quad (25)$$

$$V_S = s_1/t_{S1} \quad (26)$$

Further alternative methods and apparatus for implementing the present invention are described hereinbelow.

Figure 10:
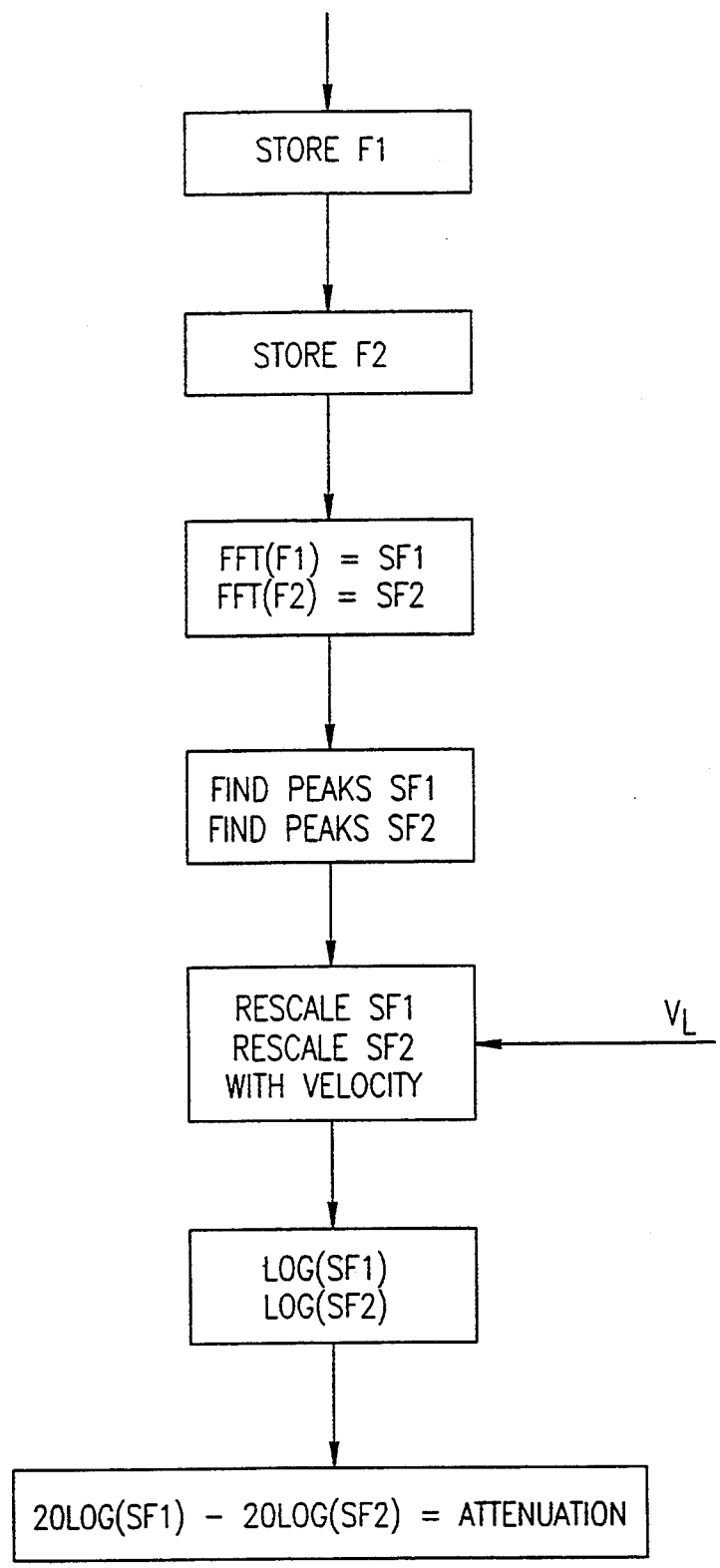
FIG. 10 is a flow chart illustration of a method of determining the attenuation of ultrasonic signals due to travel through the material.
Figure 11A:
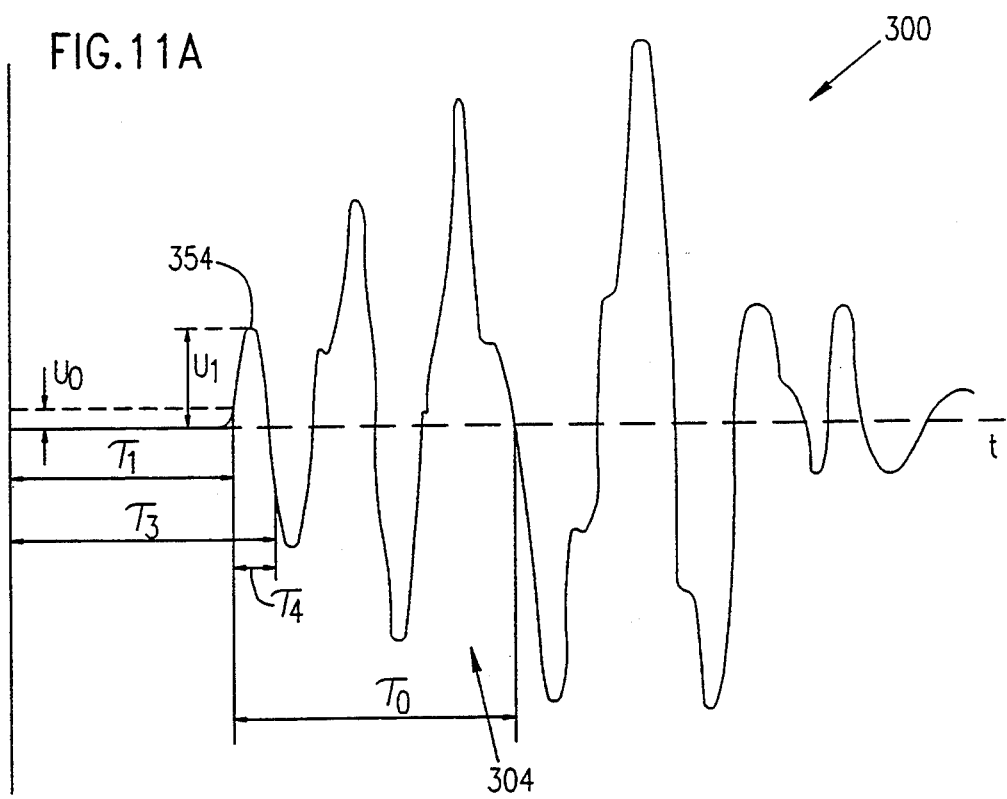
FIGS. 11A and 11B are graphical illustrations indicating output signals from the two ultrasonic receivers forming part of the apparatus of FIG. 3.
Figure 11B:
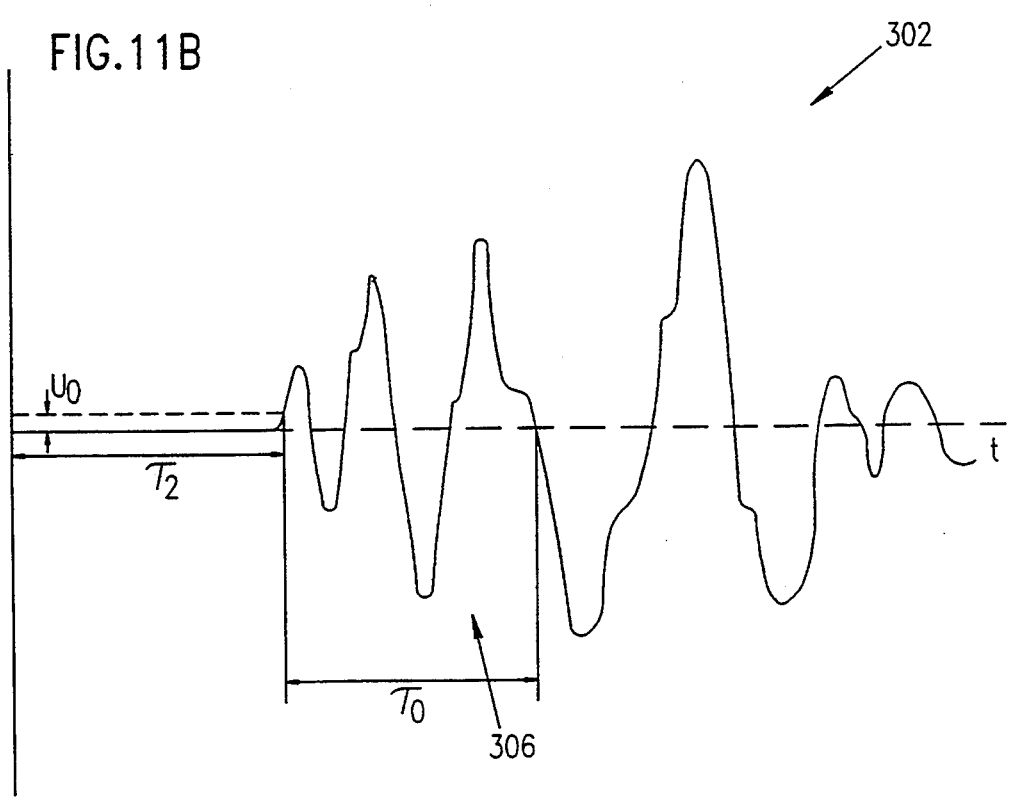
Figure 12:
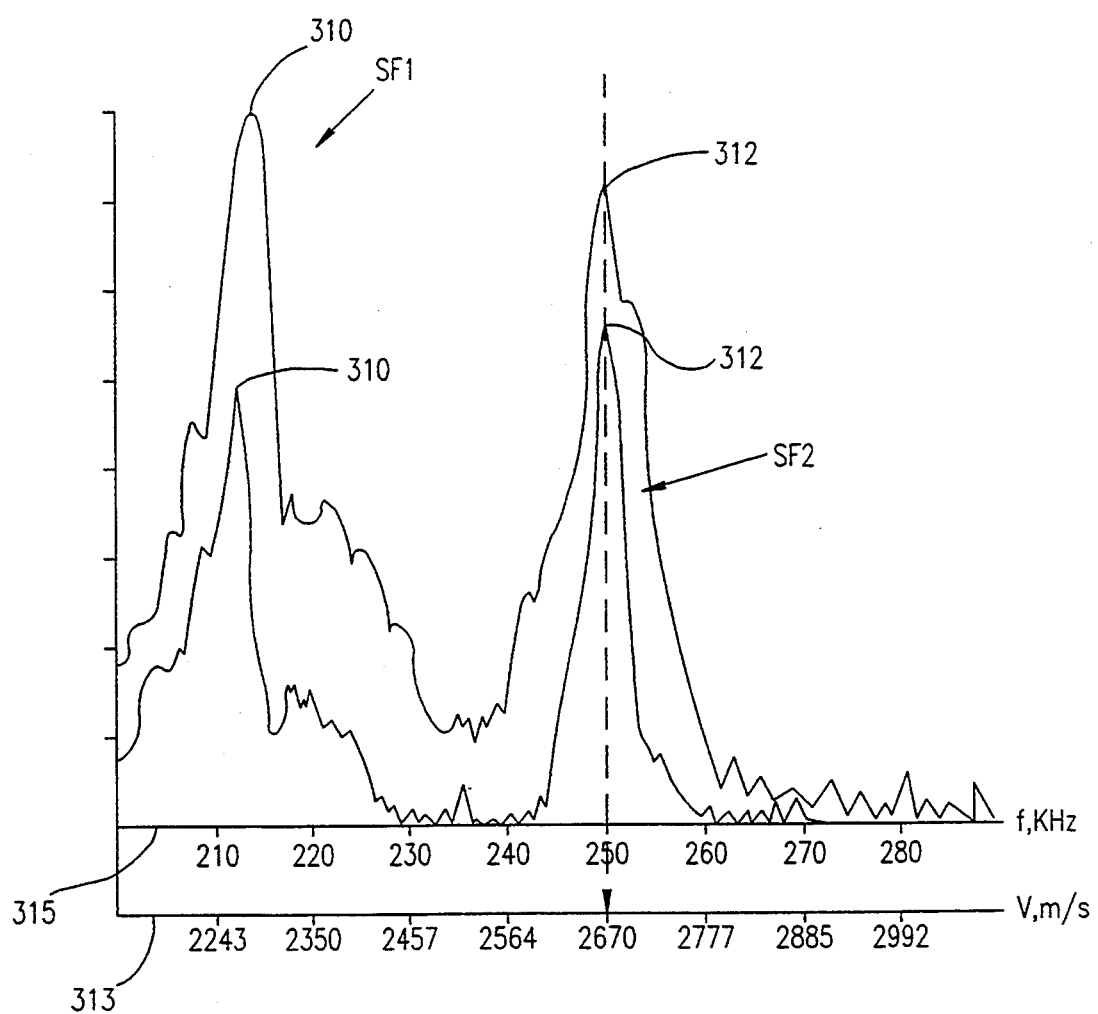
FIG. 12 is a graphical illustration of Fourier Transforms of the output signals of FIGS. 11A and 11B.
Figure 13:
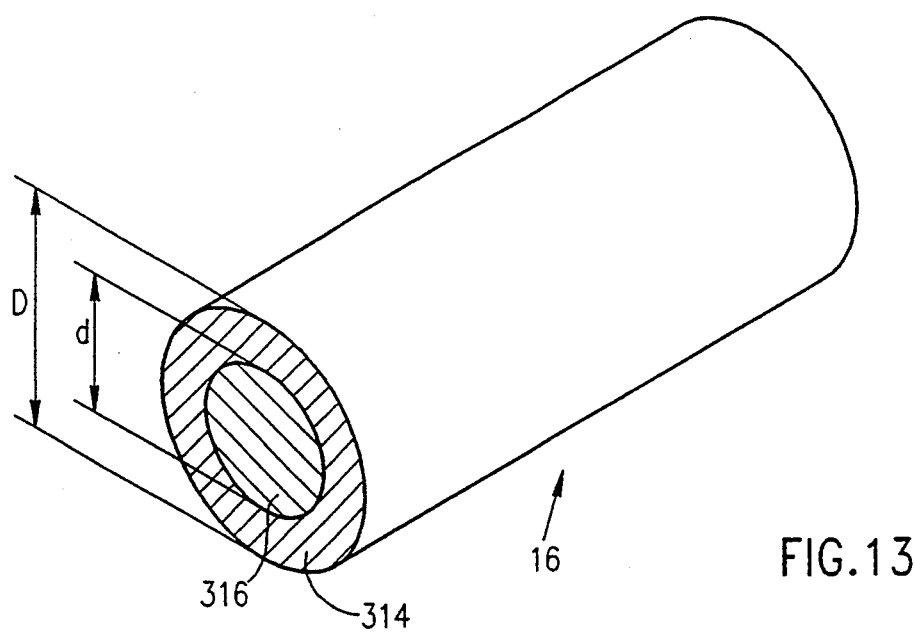
FIG. 13 is a schematic illustration of a part formed of two materials.

Reference is now made to FIG. 10 which illustrates, in flow chart format, an additional method of signal processing performed by either of the MPUs 92 and 112 and to FIGS. 11–13 which are useful in understanding the method. The method will be described in conjunction with FIG. 3, it being understood that the elements of FIG. 5 can also perform the method.

The two signal processors 86 each receive a signal from receivers 64. The first signal 300 received, shown in FIG. 11A, is received at a time $\tau_1$ after the transmitter 60 provides its input signal while the second signal 302 received, shown in FIG. 11B, arrives at a time $\tau_2$.

In this method, the signal processors 86 additionally provide to the MPU 92 portions 304 and 306 of the signals 300 and 302, respectively, each typically of $\tau_o$ seconds in length Typically, the portions 304 and 306 correspond to the initial waves which arrive at each receiver 64.

The MPU 92 or 112 stores portions 304 and 306 (denoted F1 and F2, respectively, in FIG. 10) and, when not otherwise driving the system, the MPU 92 or 112 performs a Fast Fourier Transform (FFT) on each of F1 and F2, producing signals SF1 and SF2. $\tau_o$ therefore depends on the sampling rate and the number of samples desired for use in the FFT.

Signals SF1 and SF2 are shown in FIG. 12. It is noted that they each comprise a plurality of peaks 310 and 312 and that signal SF2 is attenuated vis-a-vis signal SF1. The peaks indicate a natural filtering frequency of each of the materials which comprise the solid, wherein the frequency corresponds to the propagation speed which is the velocity at which the ultrasonic wave transmitted by transmitter 60 travels through the solid.

For solids 16 formed of two or more materials 314 and 316, such as is shown in FIG. 13, the signals SF1 and SF2 will comprise two or more peaks, respectively. The highest frequency peak 312 corresponds to the "fastest" material (i.e. the material through which the transmitted wave travels fastest) and its corresponding velocity is the velocity $V_L$ calculated by the MPU 92 in accordance with equation 9 hereinabove.

Because of the relationship between frequency velocity, the horizontal axis of FIG. 12 can be rescaled to indicate velocity. The velocity scale is indicated by reference numeral 313 and the frequency scale is indicated by reference numeral 315. The values provided are appropriate for a solid 16 comprised of the following materials: epoxy and Perspex.

The attenuation between signals SF1 and SF2 occurs because signal 302 travels through a longer portion of solid 16 than does signal 300 Thus, the attenuation corresponds to the attenuation which occurs in the portion $d_2$ of solid 16.

The method shown in FIG. 10 identifies the velocity of each of the peaks and the attenuation caused by traveling through portion $d_2$.

The method identifies the peaks 310 and 312 in each of SF1 and SF2 and matches the value for the velocity $V_L$, received from equation 9, to the last peak 312. The horizontal axis can then be rescaled and from the velocity scale 313, the velocities corresponding to the other peaks 310 can be calculated. The peak 312 corresponds to the fastest material, which, for example, is material 314.

Figure 14:
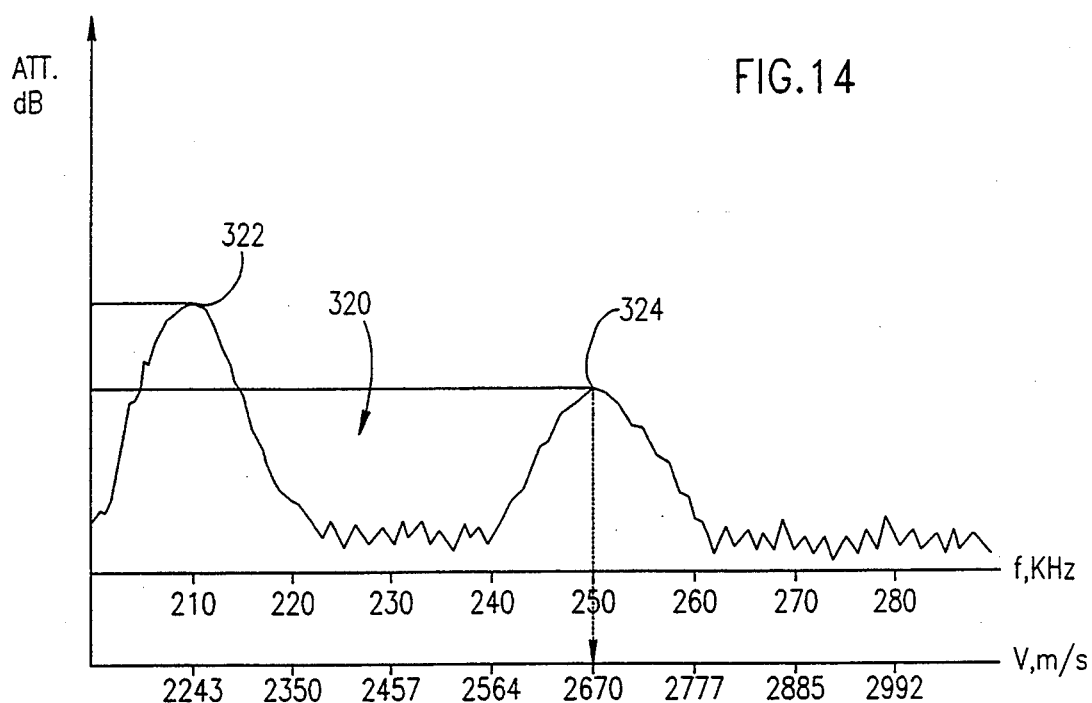
FIG. 14 is a graphical illustration of the difference between the Fourier Transforms of FIG. 12.

The method then calculates the logarithm (in base 10) of the amplitudes of each of signals SF1 and SF2 and subtracts log(SF2) from log(SF1) to produce a difference signal 320, shown in FIG. 14. The difference signal 320 typically comprises one or more peaks 322 and 324 corresponding to the peaks 310 and 312 of signals SF1 and SF2.

The amplitudes of the peaks 322 and 324 are the attenuation caused by the $d_2$ section of each of materials 316 and 314, respectively.

Figure 15:
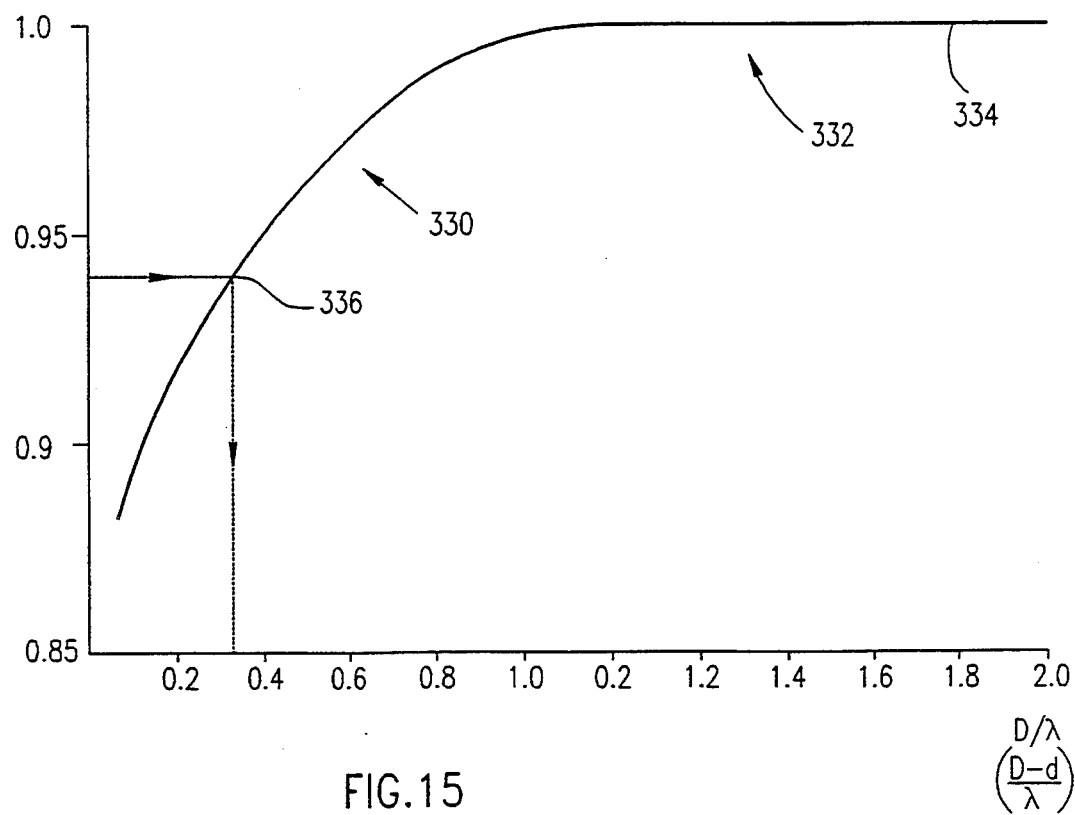
FIG. 15 is a graphical illustration of the relationship between thickness of a part and the velocity of an ultrasonic wave through the partly

In accordance with a further embodiment of the present invention, the MPU 92 estimates the thickness of the solid 16 through utilization of an empirically-derived, non-dimensional curve of normalized velocity vs. normalized thickness, as shown in FIG. 15 to which reference is now made. A discussion of the creation of the curve in FIG. 15 is discussed in the book, *Stress Waves in Solids*, written by H. Kolsky, Oxford and Clarendon Press, 1953.

The precise shape of the curve varies with the type of material being measured. However, it is has been determined by the present inventors that the shape of the curve is approximately constant over the set of human bones.

The velocity $V_L$ in the curve of FIG. 15 is normalized by the velocity $V_o$ that would be achieved in an infinite solid and the thickness is normalized by the input wavelength, lambda, of the signal from the transmitter 60. It has been determined by the inventors that the curve is approximately the same whether the thickness is the thickness D (FIG. 13) of the solid 16 or it the thickness D−d (FIG. 13) of the outside cylindrical material 314.

It is noted that the curve has a region 330, for small velocity ratios and s r all diameter/wavelength ratios and a region 332 for diameter/wavelength ratios greater than about 1.5 which is asymptotic to 1.0.

To estimate the thickness (D−d) for a solid 16, transmitter 60 is operated twice, once with a high frequency input signal and once with a low frequency input signal. For each measurement, the signal processors 84 and the MPU 92 operate, as described hereinabove with respect to FIG. 3, to determine the received velocity.

The response to the high frequency input signal, Which has a low wavelength lambda, provides a velocity datapoint 334 somewhere along the region 332 from which the velocity $V_o$ can be determined. However, the precise location of datapoint 334 is unknown since the thickness is not known.

The response to the low frequency input signal provides a velocity datapoint 336 somewhere within the region 330. Because the velocity $V_L$ is known from the measurement and the velocity $V_o$ is known from the previous measurement, the location on the curve of the datapoint 236 is known. Therefore, the ratio (D−d)/lambda can be determined. Since lambda is known from the frequency of the transmitter 60, the thickness of the solid 16, either D or (D−d), can be determined.

Figure 16:
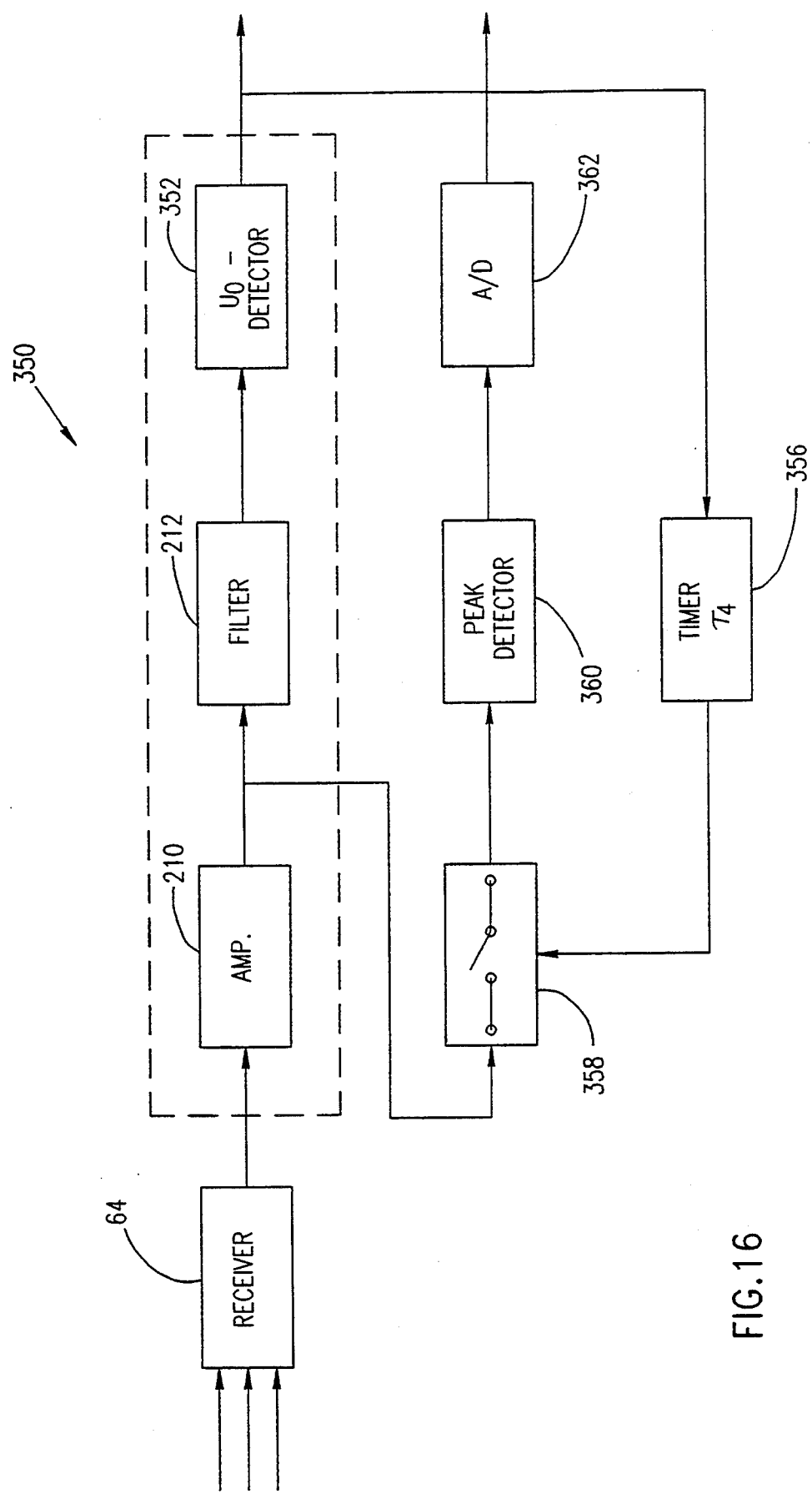
FIG. 16 is a block diagram illustration of a unit for determining attenuation from the signals shown in FIGS. 11A and 11B.

The attenuation for the faster material only can also be determined directly from the signals 300 and 302 (FIGS. 11A and 11B) by anticipating the timing of the first peak in signals 300 and 302. FIG. 16, to which reference is now made, illustrates, in block diagram format, a unit 350 for determining the attenuation. Hereinbelow characteristics of signal 300 will be discussed, it being understood that both signals 300 and 302 have these characteristics.

Figure 7:
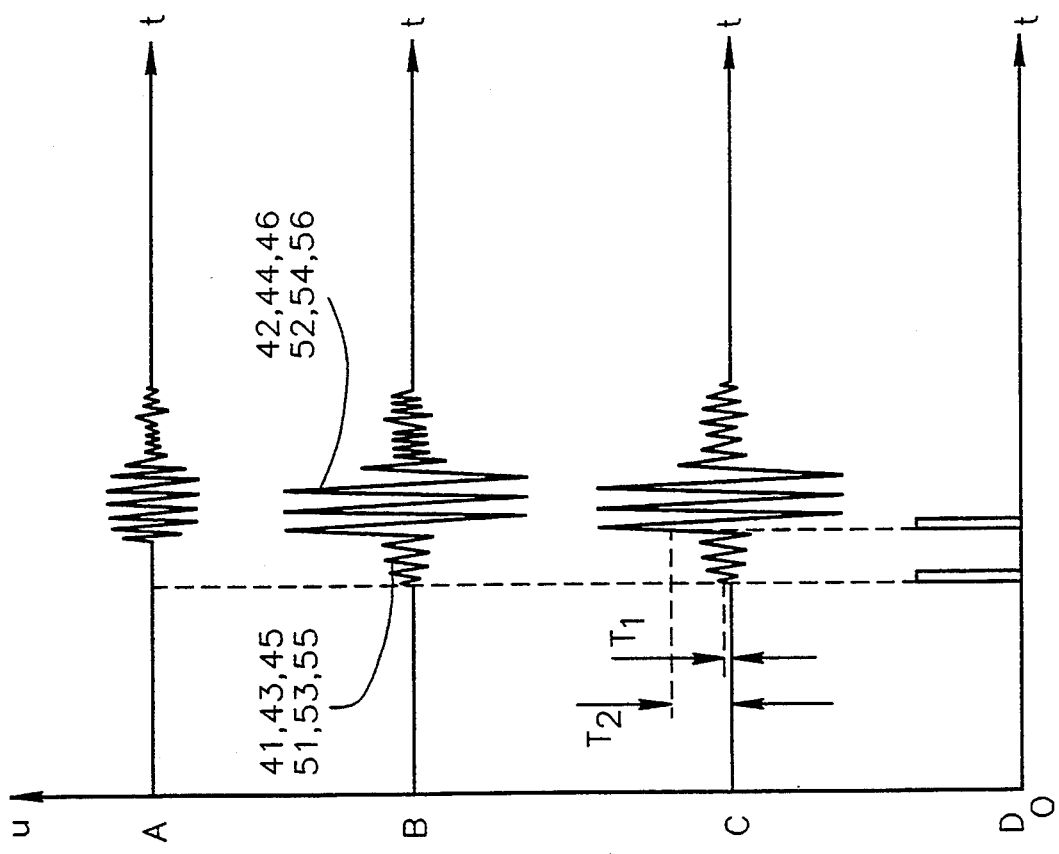
FIG. 7 is a block diagram illustration of signal processors useful in the embodiments of FIGS. 3 and 5.

Unit 350 detects a first threshold $U_0$, defined as a voltage above the expected noise level, in a manner similar to the apparatus shown in FIG. 7. Therefore, unit 350 typically comprises an amplifier, such as amplifier 210, a filter 212 and a $U_0$ detector 352, similar to threshold detector 214.

Since it is known that a first peak 354 follows after the voltage reaches the threshold level $U_0$, once $U_0$ detector 352 detects the voltage above $U_0$, it signals a timer 356 to open an analog switch 358 for a predetermined length of time $\tau_4$ during which the first peak 354 is expected to appear.

The analog switch 358 receives the output of the amplifier 210 and, while switch 358 is open, the output of amplifier 210 is provided to an analog peak detector 360 which then detects the amplitude $u_1$ of the peak 354.

The amplitude $u_1$ is provided to an analog-to-digital converter (ADC) 362 for conversion to a digital value.

The unit 350 is provided for the output of each receiver 64 and the value of $u_1$ for the first receiver 64, denoted A, is compared to that for the second receiver 64, denoted B. The ratio of the two values A and B, in dB, is the attenuation of the section of solid 16 of length $d_2$ (FIG. 1). In other words, the attenuation is:

$$\text{attenuation} = 20(\log_{10}A - \log_{10}B) \qquad (27)$$

Figure 17:
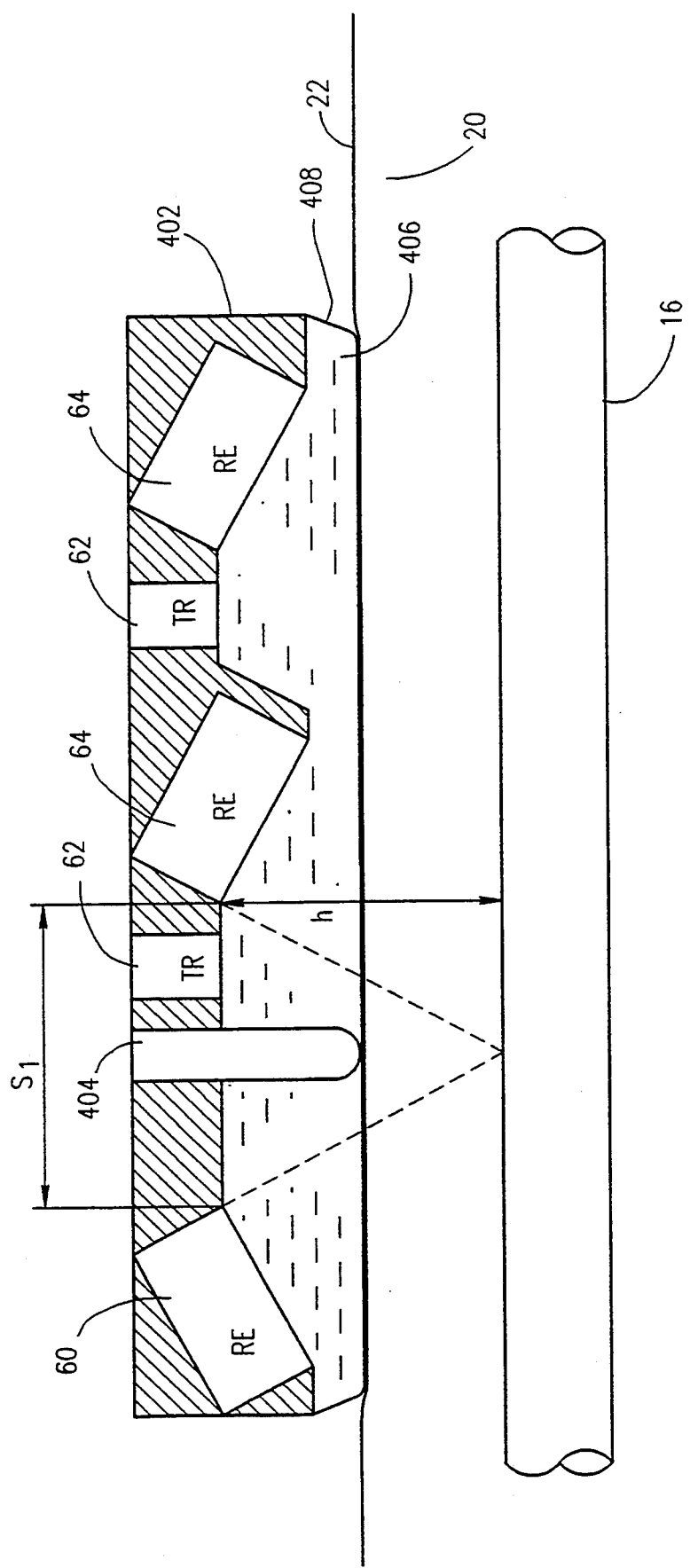
FIG. 17 is a schematic side view illustration of a transmitter and a plurality of receivers combined into a single unit.

Reference is now made to FIG. 17 which illustrates the apparatus of FIG. 3 combined into a single unit 400. Elements which are similar to those in previous embodiments have similar reference numerals.

Unit 400 comprises a holding frame 402 shaped to support the transmitter 60, the transmitter-receivers 62 and the receivers 64 at desired angles, where the angles are typically the average of the expected Brewster angles for the material to be measured. For human bone, the Brewster angle varies between 22 and 30° and thus, the angle of the receivers 64 is approximately 26°.

The ultrasonic elements 60–64 are coupled to the surface 22 of the interposed medium 20 via a coupling material 406, such as water, oil or an acoustic gel, held in place via a flexible cover 408, such as rubber. Flexible cover 408 typically is sealingly attached to holding frame 402.

Unit 400 also comprises an acoustic barrier 404, located between the transmitter 60 and the elements 62 and 64, for ensuring that generally no cross-coupling occurs between transmitter 60 and transmitter-receivers 62. Acoustic barrier 404 can be formed of any suitable material, such as rubber, and, as shown in FIG. 17, extends through the coupling material 406 to the flexible cover 408. Because of the acoustic barrier 404, the ultrasonic waves of the transmitter 60 generally only reach the receivers 64 after traveling through the interposed medium 20.

The holding frame 402 is designed to locate the transmitter 60 a distance $s_1$ from its closest receiver 64, where $s_1$ is shown in FIG. 1. As discussed previously, $s_1$ must be large enough to ensure that $d_1$ is non-negative and small enough to ensure that the received signal is large enough to measure.

It is noted that the unit 400 is operable for interposed media 20 of a given range of thicknesses, the maximum of which is the distance H from the receivers 64 to the surface 18 of the solid 16, where $H = (s_1/2)\text{ctg}\,\Theta$.

The unit 400 is typically first placed onto the surface 22 of the interposed medium 20 onto which a further coupling material (not shown) is also placed. The unit is then operated, as in previous embodiments, by rocking. The rocking will cause either or both of the coupling material 406 and the interposed medium 20 to be pressed. The coupling material ensures that the entirety of the ultrasonic elements 60–64 remain acoustically coupled with the interposed medium 20 during rocking.

Reference is now made to FIGS. 18A and 18B which respectively illustrate side and front views of an alternative embodiment of the rockable unit 68 of FIG. 4.

In this alternative embodiment, the receivers 64 and the transmitter-receivers 62 are coupled to the interposing medium 20 via a "half-bath" 420 comprised of a rubber frame 422 formed of two sections, a closed section 424 and an open section 426.

Closed section 424 encloses a coupling material, such as acoustic gel, which, is permanently enclosed therein.

The portion of rubber frame 422 which forms open section 426 ends in a circular vacuum hole 428. When the air in hole 428 is removed, a suction is created by which half-bath 420 is, attached to the surface 22 of interposed medium 20, thereby forming a sealed bath into which a coupling material, such as water, can be introduced.

The suction is created via a first pump 430 having inlet and outlet tubes 432 and a second pump 434 introduces the water into open section 426 via pipes 436. Pipes 436 are attached to circular holes 438 located above the vacuum hole 428 within the rubber frame 422.

The second pump 434 provides water, stored in a container 440, whose temperature can be regulated by a temperature regulator comprised of a heater 442 and a thermostat 444. The temperature regulation is typically incorporated when the present embodiment is placed on human skin and is operative to ensure that the water is at a temperature comfortable to humans.

As in previous embodiments the apparatus shown in FIGS. 18A and 18B is rocked to find the balance point.

Figure 19:
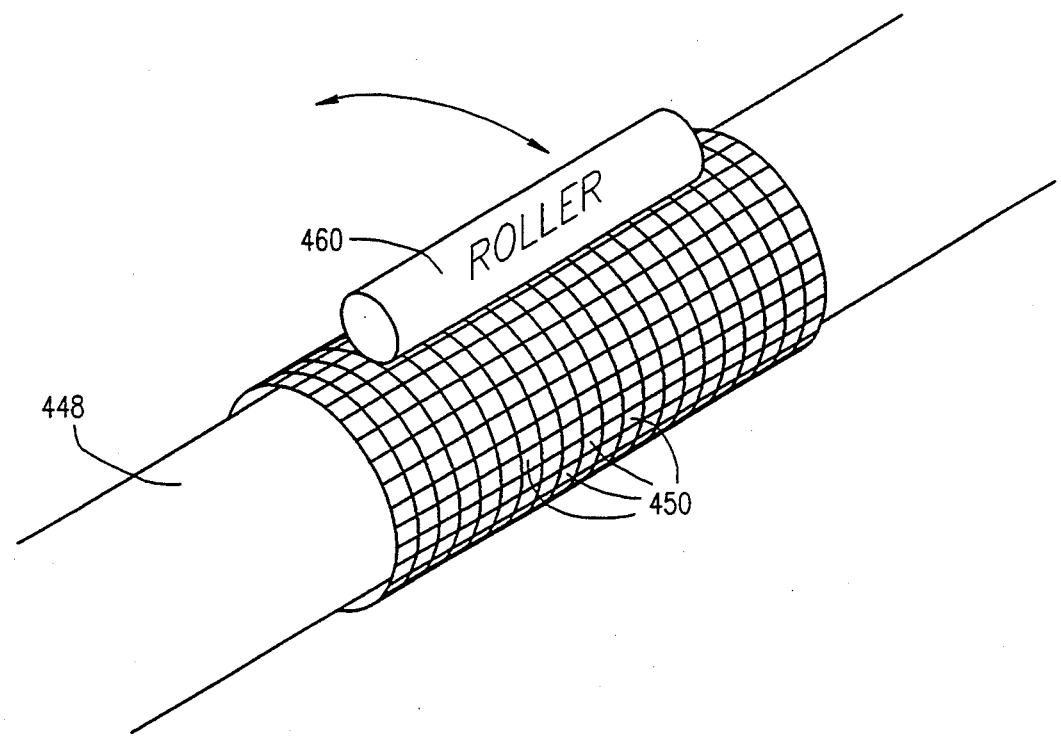
FIG. 19 is a schematic illustration of an alternative embodiment of the present invention utilizing an array of piezoelectric transducers.
Figure 20:
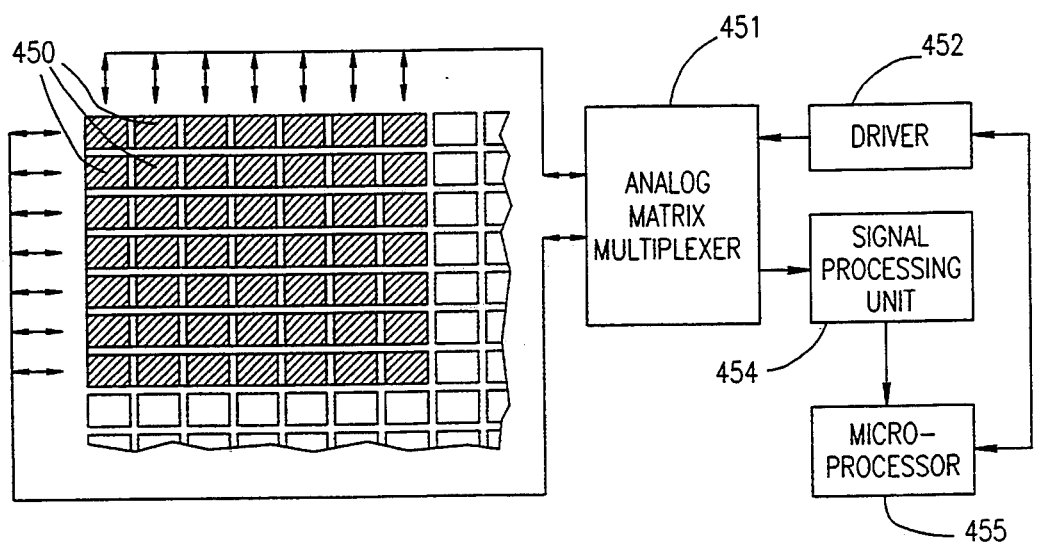
FIG. 20 is a schematic illustration of the array of FIG. 19, illustrating the connections of the transducers to controlling elements.

Reference is now made to Figs 19 and 20 which illustrate aspects of a further embodiment useful for scanning across a section 448 of a human body, such as an arm.

In this embodiment, a material formed of an array of piezoelectric cells 450, such as Kynar Piezo Film manufactured by Atochem Sensors Inc. of Valley Forge, Pa., U.S.A., is placed onto or wrapped around the section 448 or is formed into a sock-like element. The array 450 is typically acoustically coupled to the section 448 in a standard manner.

Typically, as shown in FIG. 20, the input and output wires of each piezoelectric cell 450 is connected to an analog driver matrix multiplexer 451 which, in turn, is connected to a 452 and to a signal processing unit 454. The driver 452 and unit 454 are typically controlled via a microprocessor 455.

Multiplexer 451 enables each cell 450 to be individually accessed and is operative to define each cell as a receiver, a transmitter, a transmitter-receiver or non-active.

Typically, the piezoelectric cells 450 are individually too small to form an ultrasonic transducer. Therefore, a plurality of groups of cells 450 in desired locations are electronically and selectably defined to be the ultrasonic elements 60–64.

The apparat s shown in this embodiment can be operated in many ways. For example, a roller 460, or some other suitable instrument, can be rolled across the array, pressing into the human skin in a rocking manner.

While the roller 460 is rolled, a plurality of single or groups of cells 450 are operated as transmitter-receivers 62. The receipt time outputs of the plurality of transmitter-receivers 62 are continually compared to each other and, when two receipt times match, other groups of cells 450 are temporarily operated as the transmitter 60 and the receivers 64, wherein newly-defined transmitter 60 transmits an ultrasonic wave to newly-defined receivers 64. The newly-defined transmitter 60 and receivers 64 are formed of groups of cells which are colinear with the cells 450 whose receipt times matched.

The operation described herein typically occurs within microseconds and is continually repeated while the operated rolls roller 460 across the area to be tested. It will be appreciated that the testing is not performed in any sequential order. Measurements are performed whenever two balance points are found, this being a somewhat random method of "scanning" the area to be tested.

Figure 21:
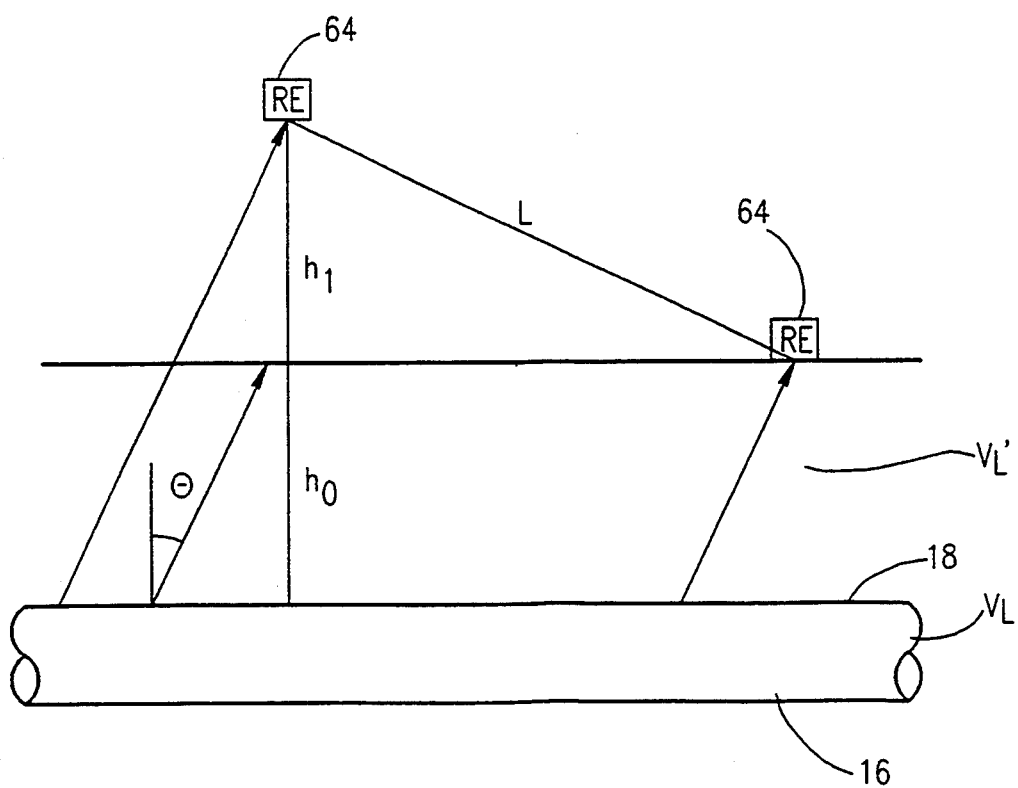
FIG. 21 is a schematic illustration of the non-parallel location of two receivers, useful in understanding calculations performed in conjunction with FIGS. 19 and 20.

Alternatively, the section 448 can be tested without the use of a roller 460 In this embodiment, groups of cells 450 are defined as transmitters 60 and receivers 64 in a sequential order across the section 448 and the velocity through the section of solid 16 thus defined is determined as described hereinbelow, with reference to FIG. 21.

The heights $h_1$ and $h_o$ are the different heights above surface 18 measured by those cells 450 defined as the transmitter-receivers 62 and L is the distance between their centers. Given the fact that t l he average velocity $V_L'$ of longitudinal ultrasonic waves through soft tissue is 1540 m/s, the value for the velocity $V_L$ of the longitudinal waves through the solid 16 can be found, as follows:

$$t_o - (t_1/2)\{\cos \Theta - (1/\sin \Theta) + \sin \Theta(\sqrt{[(2L^2/t_1^2 V_L'^2) - 1)]}\} = 0 \quad (28)$$

where:

$$t_o = t_{L2} - t_{L1} \quad (29)$$

$$t_1 2H_1/V_L' \quad (30)$$

$$\Theta = \arccos(V_L'/V_L) \quad (5)$$

Given the relationships of equations 29 and 30, equation 28 is solvable for $\Theta$, the Brewster angle, and from equation 5, the value of $V_L$ can be found. As noted hereinabove, the results from the above calculations are less accurate than those achieved via ensuring that the receipt times for the two transmitter-receivers 62 are equal.

It will be appreciated by persons skilled in the art that the present invention is not limited to what has been particularly particularly shown and described hereinabove. Rather the scope of the present invention is defined only by the claims which follow:

We claim

1. Apparatus for determining, through an interposed medium, the mechanical properties of a solid comprised of more than one material, said solid having a surface, the apparatus comprising:

an ultrasonic transmitter located in a first location for transmitting ultrasonic waves through said interposed medium and through said solid generally parallel to said surface;

a first ultrasonic receiver unit located at a second location for receiving said ultrasonic waves and a second and ultrasonic receiver unit located at a third location for receiving said ultrasonic waves, said first, second and third locations being collinear along said surface, said first, second and third locations being located such that a first receipt time of an ultrasonic wave from said surface to said first ultrasonic receiver unit at said second location is generally equivalent to a second receipt time from said surface to said second ultrasonic receiver unit at said third location;

a receiver receiving time-based output signals from said first ultrasonic receiver unit at said second location nd from said second ultrasonic receiver unit at said third location; 'circuitry for transforming the output signals to the frequency domain thereby to produce frequency domain signals; and circuitry for determining frequency values and corresponding propagation speeds for each of said materials within said solid from said frequency domain signals.

2. Apparatus according to claim 1 and also comprising circuitry for determining difference of frequency domain signals corresponding to the second nd third locations and circuitry for determining the extent of attenuation of each of said materials within said solid from said difference of said frequency domain signals.

3. A method for determining, through an interposed medium, the mechanical properties of a solid comprised of more than one material, said solid having a surface, the method comprising:

transmitting ultrasonic waves from a first location through said interposed medium and through said solid generally parallel to said surface;

receiving said ultrasonic waves with an ultrasonic receiver unit located at each of second and third location, wherein each ultrasonic receiver unit comprises at least one ultrasonic receiving transducer, and wherein said first, second, and third location are collinear along said surface;

locating said ultrasonic receiver units such that a first receipt time of an ultrasonic wave from said surface to the ultrasonic receiver unit to said second location is generally equivalent to a second receipt time from said surface to the ultrasonic receiver unit at said third location;

receiving time-based output signals from each of said ultrasonic receiver units;

transforming at least two of said output signals to the frequency domain thereby to produce frequency domain signals; and determining frequency values and corresponding propagation speeds, for each of said material within said solid from said frequency domain signals.

4. A method according to claim 3 and also including:

determining a difference of frequency domain signals corresponding to the second add third locations; and determining the extent of attenuation of each of said materials within said solid from difference of said frequency domain signals.

* * * * *